United States Patent [19]
Nielsen-Kahn et al.

[11] Patent Number: 5,972,996
[45] Date of Patent: Oct. 26, 1999

[54] 4-CYANO-4-DEFORMYLSORDARIN DERIVATIVES

[75] Inventors: Jennifer Nielsen-Kahn, East Brunswick; Bruce Tse, Edison, both of N.J.

[73] Assignee: Merck & Co., Inc., Rahway, N.J.

[21] Appl. No.: 09/123,230

[22] Filed: Jul. 28, 1998

Related U.S. Application Data

[60] Provisional application No. 60/056,819, Aug. 22, 1997.
[51] Int. Cl.$^6$ .......................... A61K 31/35; A61K 31/36; C07D 311/94; C07D 309/10
[52] U.S. Cl. .......................... 514/456; 514/460; 504/292; 549/396; 549/417; 549/418; 549/419; 549/420; 549/362
[58] Field of Search .......................... 504/292; 514/456, 514/460; 549/396, 417, 418, 419, 420, 362

[56] References Cited

U.S. PATENT DOCUMENTS 3,432,598 3/1969 Hans-Peter Sigg et al. ........... 424/122
5,854,280 12/1998 Gomez et al. ........... 514/456

FOREIGN PATENT DOCUMENTS

| 62-040292 | 2/1987 | Japan . |
| 06157582-A | 6/1994 | Japan . |
| 1162027 | 8/1969 | United Kingdom . |
| WO 96/14326 | 5/1996 | WIPO . |
| WO 96/14327 | 5/1996 | WIPO . |

OTHER PUBLICATIONS von D. Hauser, et al., Helvetica Chimica Acta—vol. 54, Fasc. 4, pp. 1178–1190, 1971.
Stephen Coval, et al., J. Antibiotics, vol. 48, pp. 1171–1172, 1995.
Lewis Mander, et al., J. Org. Chem. vol. 56, pp. 3595–3601, 1991.
Nobuo Kato, et al., J. Chem. Soc., Chem. Commun., pp. 1002–1004, 1993.

*Primary Examiner*—Ba K. Trinh
*Attorney, Agent, or Firm*—Mollie M. Yang; David L. Rose

[57] ABSTRACT

4-Cyano-4-deformylsordarin derivatives are antifungal agents useful in the treatment and/or prevention of human and animal fungal infections, as well as in the control of phytopathogenic fungi in crops.

13 Claims, No Drawings

4-CYANO-4-DEFORMYLSORDARIN DERIVATIVES

CROSS REFERENCE TO RELATED APPLICATIONS

This application is based on, and claims priority from, provisional application number 60/1056,819 filed Aug. 22, 1997.

SUMMARY OF THE INVENTION

The present invention relates to 4-cyano-4-deformylsordarin derivatives which are potent antifungal agents with a broad spectrum of activity and increased stability, to processes for their preparation, to pharmaceutical and agricultural compositions containing the compounds, and to methods of controlling fungal infections in human, animals and plant materials using such compounds.

BACKGROUND OF THE INVENTION

Sordarin is an antifungal antibiotic isolated from the mould *Sordaria araneosa* (see GB 1,162,027 and *Helvetica Chimica Acta*, 1971, 51:119–20). Other compounds having the sordarin skeleton have also been reported as antifungal agents. Japanese Kokai J62040292 discloses the compound zofimarin isolated from *Zofiela marina* sp.; Japanese Kokai J06157582 discloses the compound BE-31405 isolated from Penicillium sp.; and SCH57404 is reported in *J. Antibiotics*, 1995, 48:1171–1172. Semi-synthetic sordarin derivatives are reported in PCT Applications WO96/14326 and WO96/14327.

DETAILED DESCRIPTION OF THE INVENTION

The present invention provides compounds having the formula (I):

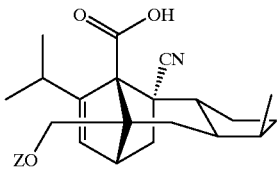

and wherein Z is a tetrahydropyrano group selected from

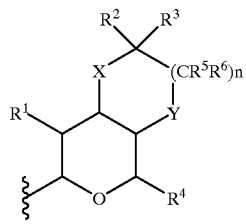

(a)

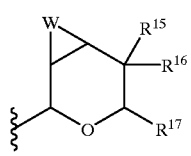

(b)

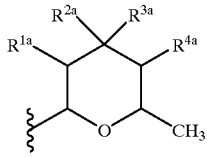

(c)

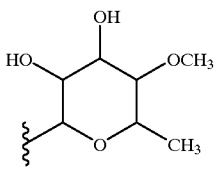

(d)

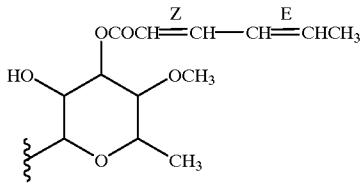

(e)

and

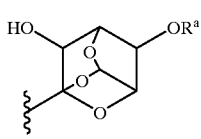

(f)

and salts and solvates (e.g. hydrates) or metabolically labile derivatives thereof,
wherein
$R^a$ is $C(O)CH_3$ or $CH_3$;
$R^1$ is hydrogen, halogen, hydroxyl, $C_{1-4}$alkoxy or acyloxy;
$R^2$ and $R^3$ are each independently hydrogen, $C_{1-6}$alkyl or $C_{1-4}$alkoxy $C_{1-4}$alkyl, or
$R^2$ and $R^3$ together with the carbon atom to which they are attached represent C=O, C=S or $C_{3-8}$cycloalkyl;
$R^4$ is hydrogen or $CH_2R^7$ (where $R^7$ is hydrogen, hydroxyl, $C_{1-4}$ alkoxy or a group $OCOR^8$ in which $R^8$ is $C_{1-4}$alkyl or aryl);
$R^5$ and $R^6$ are each independently hydrogen, $C_{1-6}$alkyl or $C_{1-4}$alkoxy $C_{1-4}$alkyl, or
$R^5$ and $R^6$ together with the carbon atom to which they are attached represent C=O, C=S or $C_{3-8}$cycloalkyl;
n is zero or 1;
X and Y are each independently oxygen, sulfur or $CR^9R^{10}$ (where $R^9$ and $R^{10}$ are each independently hydrogen, $C_{1-6}$alkyl, $C_{1-4}$ alkoxy or $C_{1-4}$alkoxy$C_{1-4}$alkyl; or $R^9$ and $R^{10}$ together with the carbon atom to which they are attached represent C=O, C=S, $C_{3-8}$ cycloalkyl or C=CHR$^{11}$ where $R^{11}$ represents hydrogen or $C_{1-4}$alkyl); or when X or Y is oxygen and n is zero then —Y—$CR^2R^3$ or —X—$CR^2R^3$— respectively may also represent —N=$CR^3$— or —$NR^{12}$—$CR^2R^3$— (where $CR^2$ and $R^3$ are C=O and $R^{12}$ is $C_{1-4}$alkyl an acyl group $COR^{13}$ where $R^{13}$ is $C_{1-6}$alkyl) or when Y is oxygen and n is zero X may be represent the group $CR^{11}$ (wherein $R^{11}$ has the meanings defined above) which is attached to the pyran ring by a double bond;
$R^{15}$ is hydrogen, halogen, azido, $C_{1-6}$alkyl, hydroxy, $C_{1-6}$alkoxy (optionally substituted by 1 or 2 hydroxy or a ketal thereof or 1 or 2 $C_{1-3}$alkoxy groups), aryl$C_{1-4}$alkoxy, $C_{3-6}$alkenyloxy, a group $OCOR^{18}$ (where $R^{18}$ is aryl$C_{1-4}$alkoxy or a $C_{1-10}$alkyl group optionally containing one or two double bonds) or $C_{1-6}$ alkoxycarbonyl $C_{1-4}$alkoxy, and $R^{16}$ represents hydrogen or $R^{15}$ and $R^{16}$ may together with the carbon atom to which they are attached represent C=O or C=CH$_2$;

$R^{17}$ is $CH_2R^{19}$ where $R^{19}$ is hydrogen, hydroxyl, $C_{1-14}$alkoxy or a group $OCOR^{20}$ in which $R^{20}$ is $C_{1-4}$alkyl); and W is oxygen, sulfur, or CH$_2$;

and the dotted line in group (a) indicates the optional presence of an additional bond;

$R^{1a}$ is hydrogen, halogen, hydroxyl or $C_{1-4}$alkoxy;

$R^{2a}$ is hydrogen, halogen, hydroxyl, $C_{1-10}$alkoxy, $C_{1-10}$alkylthio, $C_{1-6}$alkoxy$C_{1-4}$alkoxy, aryl$C_{1-6}$alkyloxy, aryl$C_{3-6}$alkenyloxy, azido, $NR^{5a}COR^{5a}$ (where each $R^{5a}$ is independently hydrogen or $C_{1-6}$alkyl), $OR^{6a}$ (where $R^{6a}$ is a cyclic ether containing 4 to 8 atoms linked to the oxygen atom via a ring carbon atom adjacent to the ring oxygen atom) or a group $Y^aC(=O)—X^a—R^{7a}$ where $Y^a$ is oxygen, sulfur or NH, $X^a$ is either a bond, an oxygen atom or a moiety $NR^{8a}$ in which $R^{8a}$ is hydrogen or $C_{1-6}$alkyl, and $R^{7a}$ is $C_{1-10}$alkyl optionally containing one or two double bonds, aryl, aryl$C_{1-4}$alkyl, aryl$C_{2-4}$alkenyl, halo$C_{1-6}$alkyl, or $C_{1-6}$alkoxy$C_{1-4}$alkyl), and $R^{3a}$ represents hydrogen, or $R^{2a}$ and $R^{3a}$ together with the carbon atom to which they are attached represent C=O or C=NOR$^{9a}$ (where $R^{9a}$ is $C_{1-6}$alkyl); and $R^4a$ is hydroxyl, $C_{1-6}$alkoxy or OC(=O)$R^{7a}$ (where $R^{7a}$ is as deemed above).

One embodiment of the present invention provides compounds of formula I wherein

Z is a)

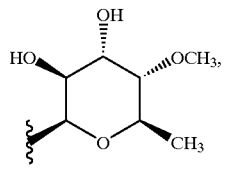

b)

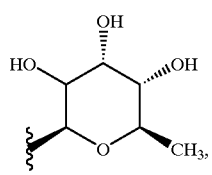

c)

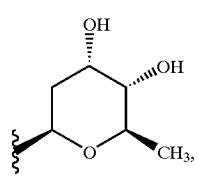

d)

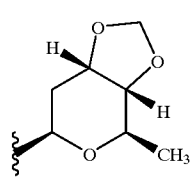

e)

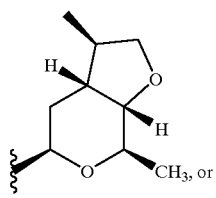

f)

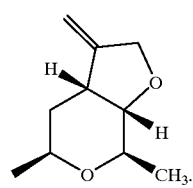

In another aspect of the present invention, there is provided a pharmaceutical composition which comprises an antifungal effective amount of a compound of formula I, and a pharmaceutically acceptable carrier. Also provided is a pharmaceutical composition which is made by combining a compound of formula I and a pharmaceutically acceptable carrier.

Another aspect of the present invention provides an agricultural composition which comprises an antifungal effective amount of a compound of formula I, and an agriculturally acceptable carrier thereof. Also provided is an agricultural composition which is made by combining a compound of formula I and an agriculturally acceptable carrier.

Yet another aspect of the present invention provides a method for treating fungal infection in an animal (including humans) which comprises administering to an animal in need of such treatment an antifungal effective amount of a compound of formula I.

A further aspect of the present invention provides a method for controlling phytopathogenic fungi in plants which comprises applying to said plant an antifungal effective amount of a compound of formula I.

In the application, unless otherwise specified, the following definitions apply:

The term "control" or "controlling" includes prophylactic use (i.e. to protect against infection) and curative use (i.e. to eradicate infection).

The term "plants" include whole live plants or parts thereof, foliage, flowers, seeds, fruits, and other materials derived from plants. The term also includes roots of the plant via application of the active ingredient to the soil.

The term "composition", as in agricultural or agrochemical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and an agriculturally acceptable carrier.

"Alkyl" as a group or part of a group means a straight or branched chain alkyl moiety such as methyl, ethyl, n-propyl, n-butyl, isopropyl, s-butyl, t-butyl, n-hexyl and n-octyl.

"Aryl" as a group or part of a group means phenyl or heteroaryl each optionally substituted by one to three groups independently selected from halogen, hydroxyl, $C_{1-6}$alkyl, $C_{1-6}$alkoxy or $C_{1-4}$alkoxycarbonyl. The heteroaryl group may be a 5- or 6-membered heteroaromatic ring containing one or more heteroatoms selected from nitrogen, oxygen and sulfur. Suitable examples of heteroaryl groups include pyridyl, furyl, thienyl and pyrrolyl.

"Halogen" or "halo" means fluorine, chlorine, bromine or iodine.

When $R^1$ is an acyloxy group it may represent, for example a group $OCOR^{13}$ where $R^{13}$ is as defined above.

Suitable salts of a compound of formula I include inorganic base salts such as alkali metal salt (e.g. sodium and potassium salts), ammonium salts, and organic base salts. Suitable organic base salts include amine salts such as trialkylamine (e.g. triethylamine), dialkylamine salts (e.g. dicyclohexylamine), optionally substituted benzylamine (e.g. phenylbenzylamine or p-bromobenzylamine), ethanolamine, diethanolamine, N-methylglucosamine, N-methylpiperidine, pyridine and substituted pyridine (e.g. collidine, lutidine, 4-dimethylaminopyridine), and tri(hydroxymethyl)methylamine salts, and amino acid salts (e.g. lysine or arginine salts).

Metabolically labile derivatives of compounds of formula I are compounds which are converted in the subject being treated (be it an animal, a plant (including foliage, flower, fruit, seed, or other parts or product of the plant), or soil) into compounds of formula I. Examples of such derivatives include conventional metabolically labile esters formed from the carboxylic acid in the molecule.

Preparation of Compounds. Compounds of formula I may be prepared from sordarin and derivatives thereof, sordaricin, and other sordarin type compounds, which all have been described in the literature.

Sordarin is [1R-(1α,3aβ,4β,4aβ,7β,7aα,8aβ)] 8a-[(6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid having the formula II:

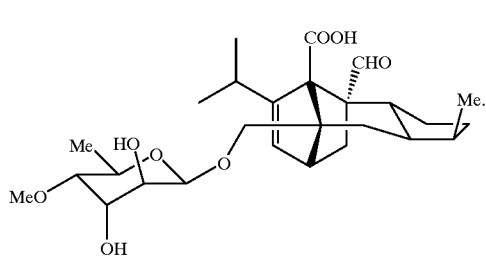

(II)

Sordarin can be obtained by the cultivation of *Sodaria araneosa* NRRL 3196 (also deposited with the ATCC as ATCC 36386) according to the procedure described in GB1,162,027 or in WO96/14326. Sordarin can also be isolated from the fermentation of *Rosellinia subiculata* and an unidentified fungus ATCC 74387 as described hereinbelow.

Zofimarin may be obtained from the fermentation broth of *Zofiela marina* SANK 21274 (ATCC 34456) as described in Japanese Kokai 62040292. BE31405 (I, wherein A is (f) and $R^a$ is acetyl) is produced by Penicillum sp. F31405 as described in Japanese Kokai 06157582. $SCH_{57404}$ (I, wherein A is (f) and $R^a$ is methyl) is produced by a fungus identified as Schering culture number SCF1082A as reported in *J. Antibiotics*, 1995, 48(10):1171–1172.

Starting materials for sordarin derivatives (I, wherein Z is (a) or (b)), are described in PCT Application WO96/14326; and starting materials for sordarin derivatives (I, wherein Z is (c)) are described in PCT Application WO96/14327.

Sordaricin (VI) is [1R-(1α,3aβ,4β,4aβ,7β,7aα,8aβ)] 4-formyl-8a-(hydroxymethyl)-4,4a,5,6,7,7a,8,8a-octahydro-7-methyl-3-(1-methylethyl)-1,4-methano-s-indacene-3a(1H)-carboxylic acid having the formula VI:

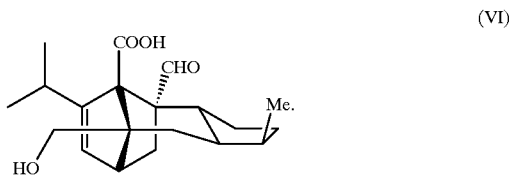

(VI)

Sordaricin can be prepared from sordarin by treatment with concentrated hydrochloric acid. As disclosed in WO96/14326 sordaricin is also obtained from fermentation of a mutant derived from *Sordaria araneosa* NRRL 3196, and by biotransformation of sordarin using a Coryneform species.

As mentioned above, two other organisms have been found to produce sordarin.

One of the fungal strains used to produce sordarin is an unidentified sterile fungus GB3109 that was isolated from the internal tissues of roots of a mangrove shrub, *Conocarpus erectus* (Combretaceae), collected in the Manglar de Réo Rincón, Península de Osa, Provincia de Puntarenas, Costa Rica, and identified as MF6232 in the culture collection of Merck & Co., Inc., Rahway, N.J. This culture was deposited on Aug. 27, 1996 in the permanent collection at the American Type Culture Collection, 12301 Parklawn Drive, Rockville, Md. 20852, USA under the terms of The Budapest Treaty on the International Recognition of the Deposit of Microorganisms for the Purposes of Patent Procedure, and assigned the accession number ATCC 74387.

The fungus was grown on a variety of mycological media, under different light regimes, and on sterilized leaves and filter paper but in all cases, it has failed to produce reproductive structures and thus cannot be identified.

In agar culture, colonies of the fungus exhibit the following morphology:

Colonies on oatmeal agar (Difco) at 23° C., 12 hr photoperiod, growing moderately fast, attaining 85–90 mm in 14 days, with advancing zone appressed, even, obscurely zonate, strongly radially striate, with moist appressed mycelium at the center, becoming silky with radiating prostrate hyphal bundles or strands, translucent to pale pink, near Pale Ochraceous Salmon (capitalized color names from Ridgway, R. 1912. Color Standards and Nomenclature, Washington, D.C.), Light Ochraceous Salmon, pinkish gray Avellaneous, Cinnamon-Drab, or white in uppermost aerial mycelium, reverse pale pinkish gray, exudates absent, odor faintly fragrant. No growth at 37 C on oatmeal agar.

Colonies on V8 juice agar (Stevens, R. B. 1981. Mycology Guidebook. University of Washington Press, Seattle, pg. 665) at 23° C., 12 hr photoperiod, growing slowly attaining 37–42 mm in 14 days, submerged to at the margin, mostly with appressed most mycelium, with some scant floccose aerial mycelium towards outer third, zonate, translucent to pale grayish pink, similar to color on oatmeal agar, reverse translucent to pale reddish brown, near Wood Brown, Fawn Color.

Colonies on cornmeal agar (Difco) at 25° C., 12 hr photoperiod, growing slowly, attaining 33–34 mm in 14 days, with margin submerged, lacking aerial hyphae, zonate, translucent.

The mycelium is composed of highly branched, simple septate, hyaline hyphae.

The second fungal strain (GB3719) used to produce sordarin is a strain of *Rosellina subiculata* (Ascomycotina, Xylariaceae), designated as MF6239 in the culture collection of Merck & Co., Inc., Rahway, N.J. This culture was deposited on Aug. 27, 1996 in the permanent collection at the American Type Culture Collection, 12301 Parklawn Drive, Rockville, Md. 20852, USA under the terms of The Budapest Treaty on the International Recognition of the Deposit of Microorganisms for the Purposes of Patent Procedure, and assigned the accession number ATCC 74386.

Ascomata of *Rosellinia subiculata* (GB3719) were found on a decorticated hardwood limb on the shore of the Navesink River, Monmouth Co., N.J. In the laboratory, the apices of several ascomata were removed with a sterilized microtome blade and asci, paraphyses and ascospores from the centrum were removed with an insect pin and streaked onto malt-yeast extract agar. Ascospores were incubated overnight until they germinated and were transferred to tubes of malt-yeast extract agar to initiate pure colonies.

The morphology of *Rosellinia subiculata* (GB3719) generally conformed to descriptions in the literature (J. B. Ellis & B. M. Everhart. 1892. The North American Pyrenomycetes. Published by the authors, Newfield, N.J. pg. 165–166; L. E. Petrini. 1993. Rosellinia species of the temperate zones. Sydowia 44:169–281). The key features that lead to identification of the fungus as *Rosellinia subiculata* were: stromatic ascomata occurring singly but aggregated or fused in small clusters on a mycelial subiculum on decorticated wood; stromata were hemispherical, papillate, smooth, shiny, black, subiculum a thin mycelial mat, pale buff, or sometimes appearing only as a lightly colored discoloration of the wood adjacent to the stromata; asci were cylindrical with an amyloid apical plug; ascospores were brownish gray, broadly elliptical to slightly reniform, smooth, without appendages or sheaths, with a straight, ventral germ slit, 10–12×5–6 $\mu$m.

In agar culture, colonies of the fungus exhibit the following morphology:

Colonies on oatmeal agar at 23° C., 12 hr photoperiod, growing moderately fast, attaining 73–75 mm in 14 days, with advancing zone appressed, even, obscurely zonate, with white velvety to floccose mycelium over inner third, with moist appressed mycelium over outer two-thirds, translucent to white or pale pink, pale vinaceous pink, Light Vinaceous Cinnamon in reverse, exudates absent, slightly fragrant odor. No growth at 37 C on oatmeal agar.

Colonies on V8 juice agar at 23° C., 12 hr photoperiod, growing slowly attaining 25–35 mm in 14 days, submerged at the margin, mostly with appressed most mycelium, with some floccose aerial mycelium towards inner third, zonate, translucent to pale grayish pink, Vinaceous Cinnamon, reverse translucent to cinnamon, Orange-Cinnamon, Cinnamon, or pale reddish brown, Russet, Fawn Color, odor fragrant.

Colonies on cornmeal agar at 25° C., 12 hr photoperiod, growing slowly, attaining 29–34 mm in 14 days, with margin submerged, lacking aerial hyphae, azonate, translucent, or with scant white mycelium at inoculation point, colorless in reverse.

When first grown in culture in August of 1993, the strain produced scant conidiophores and conidia of a Geniculosporium anamorph similar to that described by Petrini 1993. However, sporulation is no longer apparent, most likely due to prolonged storage and repeated transfers. At least in one case, a few mature perithecia with asci and ascospores identical to those observed in nature were formed after 5 weeks growth on oatmeal agar. Ascospores germinated overnight when incubated on malt-yeast extract agar at rom temperature. The mycelium is composed of highly branched, simple septate, hyaline hyphae.

Sordarin is produced by cultivating a strain of *Rosellina subiculata* or the unidentified fungus MF6232 (ATCC$_{74387}$) capable of producing said compound on a conventional solid medium or in a conventional aqueous medium. The organism is grown in a nutrient medium containing known nutritional sources for similar fungi, i.e. assimilable sources of carbon and nitrogen plus optional inorganic salts and other known growth factors. The general procedures used for the cultivation of other similar fungi are applicable to the present invention.

The nutrient medium should contain an appropriate assimilable carbon source such as ribose, glucose, sucrose, cellobiose or fructose. As nitrogen source, ammonium chloride, ammonium-sulfate, urea, ammonium nitrate, sodium nitrate, etc. may be used either alone or in combination with organic nitrogen sources such as peptone, fish meal extract, yeast extract, corn steep liquor, soybean powder, cotton seed flour, etc. There may also be added, if necessary, nutrient inorganic salts to provide sources of sodium, potassium, calcium, anammonium, phosphate, sulfate, chloride, bromide, carbonate, zinc, magnesium, manganese, cobalt, iron, and the like.

Production of sordarin may be effected at any temperature conducive to satisfactory growth of the producing organism, e.g. 20°30° C. Ordinarily, optimum production of the desired compound is obtained in shake flasks after incubation periods of 7–21 days. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from slant culture, lyophilized culture or frozen culture of the organism. After obtaining an active inoculum in this manner, it is aseptically transferred to the fermentation tank medium. Production of the desired compound in tank fermentors usually reaches the optimum after 7 to 21 days of incubation. Agitation in the tank fermentor is provided by stirring and aeration may be achieved by injection of air or oxygen into the agitated mixture. Compound production may be monitored using chromatographic or spectroscopic techniques, or by a conventional biological assay.

Sordarin is readily recovered from fermentation broth by extracting the whole broth with an organic solvent such as methyl ethyl ketone. The compounds may be purified using standard methods well known in the art such as gel filtration chromatography, thin layer chromatography, high performance liquid chromatography, concentration, precipitation and/or crystallization, or combinations thereof. Alternatively, the whole broth or an organic extract thereof may be spray-dried or freeze-dried, followed by purification as above mentioned.

The compounds of the present invention (formula I) may be prepared by the processes described below. The conditions are representative and are not intended to be limiting.

As illustrated in Scheme 1, compounds of Formula I where Z is (a) or (b) may be prepared from starting materials described in PCT Application WO96/14326 or from starting materials described in PCT Application WO96/14327 for compounds of Formula I where Z is (c). The carboxylic acid of the starting material is derivatized with a suitable protecting group (i.e. benzyl or p-methoxybenzyl) and an aldoxime is formed by treatment with hydroxylamine hydrochloride in an alcoholic solvent containing pyridine. The aldoxime is transformed into a nitrile group with a suitable dehydrating agent (i.e. (methoxycarbonylsulfamoyl)-triethylammonium hydroxide inner salt or cyanuric chloride) and the protecting group is removed to yield a compound of formula (I).

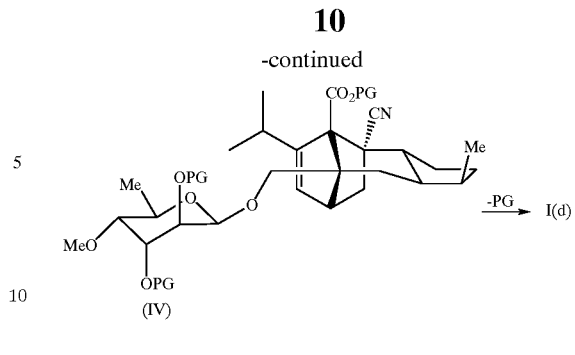

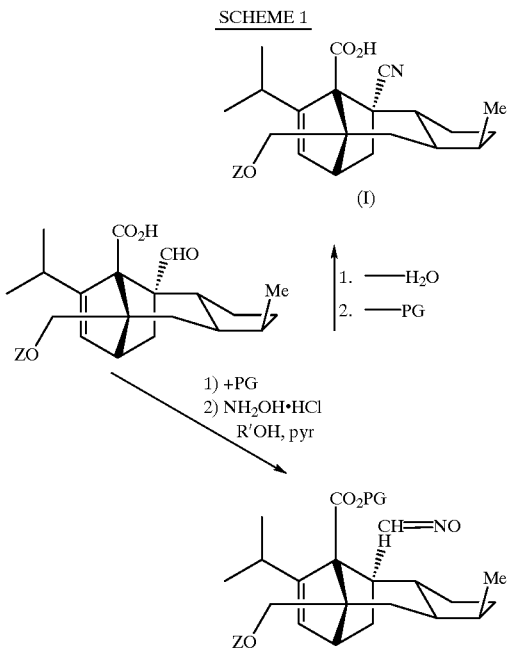

A compound of formula I(d) may be prepared as illustrated in Scheme 2. Sordarin is suitably protected and the aldehyde is reacted with hydroxylamine hydrochloride in an alcoholic solvent in the presence of pyridine. The resultant aldoxime is dehydrated with a reagent such as (methoxycarbonylsulfamoyl)-triethylammonium hydroxide inner salt or cyanuric chloride to give the nitrile compound (IV). Removal of the protecting groups (PG) gives the compound of formula I(d).

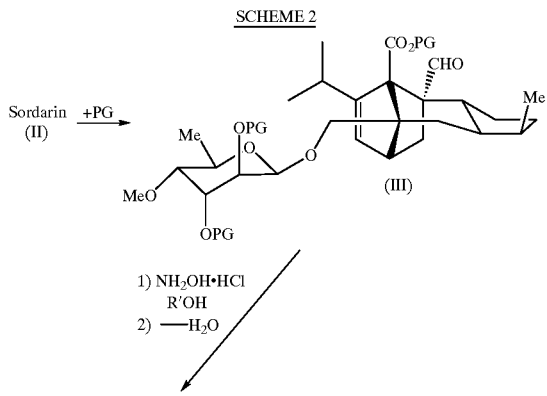

Scheme 3 shows the microbial demethylation of the 4'-methoxy group of compound I(d) to provide Compound (V). The demethylation is accomplished by contacting a compound of formula I(d) with a culture of a strain of *Streptomyces avermitilis* in a fermentation medium containing assimilable sources of carbon and nitrogen; and isolating compound (V) from the fermentation medium. Suitable strains of *Streptomyces avermitilis* includes strain MA4848 deposited at American Type Culture Collection, Rockville, Md. as ATCC 31272. Compound (V) may be employed in the synthesis of compounds of formula (I).

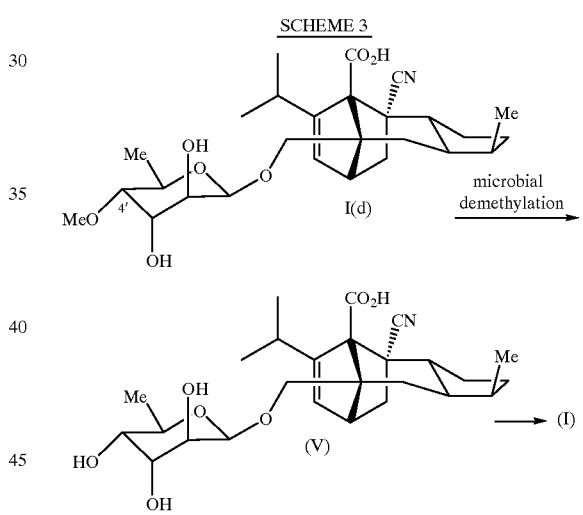

Alternatively, as shown in Scheme 4, sordaricin (VI) may be employed as a starting material for the synthesis of compounds of formula (I). Derivatization of the carboxylic acid with a suitable protecting group followed by protection of the primary hydroxyl group allows the synthesis of the nitrile-aglycone compound (VII) by reaction with hydroxylamine hydrochloride followed by dehydration and removal of the hydroxy protecting group. Attachment of a suitable sugar or modified sugar substrate by methods known to those skilled in the art, provide compounds of formula (I).

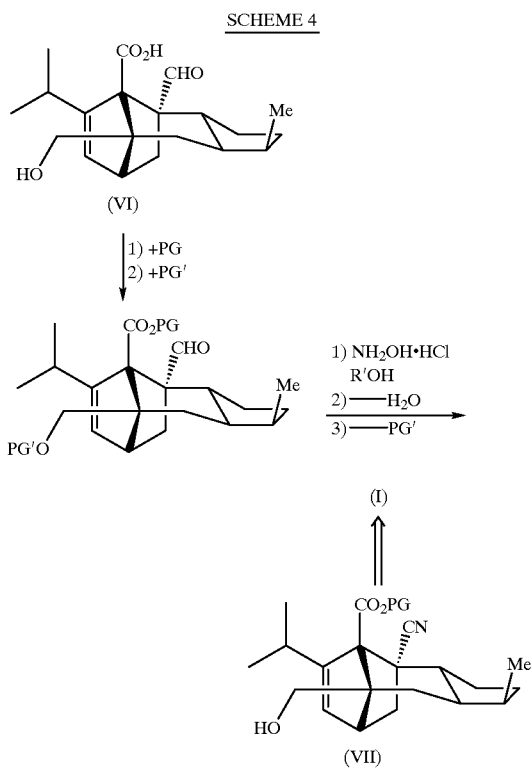

SCHEME 4

Utility. Compounds of formula I are antifungal agents useful as human and animal medicaments, as well as crop protectants.

The compounds of formula I are very active fungicides useful in combating fungal infections in animals, including humans. For example, they may be used in the treatment of fungal infections caused by organisms such as species of Candida (e.g. *Candida albicans, Candida glabrata,* (*Torulopsis glabrata*), *Candida tropicalis,* and *Candida pseudotropicalis*), *Cryptococcus neoformans, Pneumocystis carinii,* Aspergillus Sp (e.g. *Aspergillus flavus* and *Aspergillus fumigatus*), Coccidioides (e.g. *Coccidioides immitis*), Paracoccidioides (e.g. *Paracoccidioides brasiliensis*), Histoplasma (e.g. *Histoplasma capsulatum*) or Blastomyces (e.g. *Blastomyces dermatitidis*). They may also be used to treat other fungal infections caused by species of Trichophyton, Microsporum or Epidermophyton (e.g. *Trichophyton mentographytes, Trichophyton rubrum, Microsporum canis* or *Epidermophyton floccosum*), or in mucosal infections caused by *Candida albicans*.

Compounds of formula I may also be used to treat other infections caused by species of filamentous fungi such as Geotrichum (e.g. *Geotrichum clavatum*), Trichosporon (e.g. *Trichosporon beiglii*), Blastoschizomyces (e.g. *Blastoschizomyces capitatus*), Sporothrix (e.g. *Sporothrix schenckii*), Scedosporium (e.g. *Scedosporium apiosperum*), Cladosporium (e.g. *Cladosporium carrionii*) and *Pityrosporum ovale*.

The compounds of formula I may also be used to treat infections caused by protozoa such as Toxoplasma, Cryptosporidium, Leishmania, Tripanosoma, Giardia and Trichomonas.

The in vitro evaluation of the anti-fungal activity of compounds of the invention was performed on liquid or solid medium by the anti-fungal two-fold serial dilution technique of determining the minimum inhibitory concentration (MIC) of anti-fungal agent that inhibited development of growth after 24 to 48 hours of incubation at 35° C. In practice, a series of agar plates or broth microdilution panels containing two-fold dilutions of anti-fungal agent tested were inoculated with a standard culture of a clinically relevant pathogen, for example, *Candida albicans*. The agar plates or broth microdilution panels were then examined for the presence or absence of growth of the fungus and the appropriate MIC values were noted. Visualization of endpoints was assisted by employment of the vital stain Alamar Blue.

The in vivo evaluation of compounds of formula I can be carried out at a series of dose levels by administration (e.g. subcutaneously, orally, intraperitoneally or intravenously) to mice inoculated intravenously with a strain of Candida spp. The kidneys of the test animals may be removed and quantitated for viable Candida spp. and the reduction in infection may be determined relative to untreated control animals.

In view of their antifungal activity, compounds of formula I are useful for the treatment and/or prevention of a variety of fungal infections in human beings and animals. Such infections include superficial, cutaneous, subcutaneous and systemic mycotic infections such as respiratory tract infections, gastrointestinal tract infections, cardiovascular infections, urinary tract infections, CNS infections, candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityriasis versicolor, erythrasma, intertrigo, fungal diaper rash, candida vulvitis, candida balanitis and otitis externa. They may also be used as prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states.

Compounds of formula I also have use as broad spectrum crop antifungal agents and are effective on a broad spectrum of phytopathogenic fungi, in particular those from the class consisting of: Deuteromycetes (e.g. Botrytis spp., Septoria spp., Pyricularia spp., Stagnospora spp., Helminthosporium spp., Fusarium spp., Cercospora spp., Rhynchosporium, spp. Pseudocercosporella, spp. and Alternaria spp.); Basidiomycetes (e.g. Puccinia spp., Rhizoctonia spp., and Hemileia); Ascomycetes (e.g. Venturia spp., Podospharera spp., Erysiphe spp., Monilinia spp. and Uncinula spp.); and Oomycetes (e.g. Phytophthora spp., Pemospora spp., Bremia spp., Pythium spp., and Plasmopara spp.). The foregoing list exemplifies the phytopathogenic fungi against which the named compounds demonstrate activity, and is not limiting in any manner. These compounds have very advantageous curative and preventive fungicidal properties for protecting plants, and can be used to inhibit or to destroy the microorganisms occurring on plants or on parts of plants (the fruit, blossom, leaves, stalks, tubers or roots) of different crops of useful plants, while at the same time parts of plants that grow later are also protected against such microorganisms. They can also be used as dressings in the treatment of plant propagation material, especially seed (fruit, tubers, grain) and plant cuttings (for example rice), to provide protection against fungal infections and against phytopathogenic fungi occurring in the soil. Compounds of formula I of the invention are distinguished by the fact that they are especially well tolerated by plants and are environmentally friendly.

Agricultural evaluation of compounds of formula I can be carried out using the following tests.

1. Action against *Erysiphe graminis* on wheat.

a) After 1 week cultivation, wheat plants are sprayed to run off with a spray mixture (200 ppm active ingredient/20% acetone/0.25% Triton X155). After 2 hours, the treated plants are infected with ascospores shaken from inoculum plants. Fungal attack is evaluated after incubation for 8 days at 22° C. at 50% relative humidity to determine the protection given by the compound.

b) After 1 weeks cultivation, wheat plants are infected with ascospores shaken from inoculum plants. After 24 hours, the wheat plants are sprayed with a spray mixture (200 ppm active ingredient/20% acetone/0.25% Triton X155). Fungal attack is evaluated after incubation for 8 days at 22° C. at 50% relative humidity to determine the degree of curative activity provided by the compound.

c) After 1 weeks cultivation, wheat plants are infected with ascospores shaken from inoculum plants. After 24 hours, the soil in which the wheat plants are growing is drenched with the drench mixture (200 ppm active ingredient/20% acetone/0.25% Triton X155). Fungal attack is evaluated after incubation for 8 days at 22° C. at 50% relative humidity to determine the degree of curative activity provided by the compound.

2. Action against *Puccinia recondita* on wheat a) After 1 weeks cultivation, wheat plants sprayed to run off with a spray mixture (200 ppm active ingredient/20% acetone/0.25% Triton X155). After 2 hours, the treated plants are infected with a spore. Fungal attack is evaluated after incubation for 1 day at 95–100% relative humidity at 20° C. followed by 7 days at 25° C. at 50% relative humidity to determine the protection given by the compound.

b) After 1 weeks cultivation, wheat plants are infected with a spore suspension After 24 hours, the infected plants are sprayed to run off with a spray mixture (200 ppm active ingredient/20% acetone/0.25% Triton X155. Fungal attack is evaluated after incubation for 1 day at 95–100% relative humidity at 20° C. followed by 7 days at 25° C. at 50% relative humidity to determine the degree of curative activity provided by the compound.

c). After 1 weeks cultivation, wheat plants are infected with a spore suspension After 24 hours, the soil in which the wheat plants are growing was drenched with the drench mixture (200 ppm active ingredient/20% acetone/0.25% Triton X155). Fungal attack is evaluated after incubation for 1 day at 95–100% relative humidity at 20° C. followed by 7 days at 25° C. at 50% relative humidity to determine the degree of curative activity provided by the compound.

Based on the spectrum of activity, the compounds of the present invention can be used to protect or cure plants of phytopathogenic fungi affecting various useful crops. The following species of plants are suitable for the use described in the scope of the invention of the stated compounds: cereal (e.g. wheat, rye, oat, barley, rice, sorghum and related crops); beet (sugar beet and fodder beet); pomes, dropes and soft fruit (e.g. apples, pears, plums, peaches, almonds, cherries, strawberries, raspberries, and blackberries); leguminous plants (e.g. beans, peas, lentils and soybeans); oil plants (rape, mustard, poppy, olives, sunflowers, coconut, castor oil plants, cocoa beans and groundnuts); curbitats (e.g. cucumber, squash, and melon); fiber plants (e.g. cotton, flax, hemp, and jute); citrus fruit (e.g. oranges, lemons, madarins and grapefruit); vegetables (e.g. lettuce, cabbage, spinach, carrot, asparagus, paprika, onions, tomatoes, and potatoes); lauraceae: (avocados, cinnamon and camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). However, the aforementioned plant species do not constitute a limiting list of plants with respect to spectrum by the stated compounds.

The compounds of formula I are particularly useful for controlling the following plant diseases:

*Erysiphe graminis* in cereals, *Erysiphe cichoracearum* and *Sphaerotheca fuliginea* in cucurbits, *Podosphaera leucotricha* in apples, *Uncinula necator* in vines, Puccinia species in cereals, *Rhizoctonia solani* in cotton, Ustilago species in cereals and sugar cane, *Venturia inaequalis* (scab) in apples, Helminthosporium species in cereals, *Septoria nodorum* in wheat, *Botrytis cinerea* (gray mold) in strawberries and grapes, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in various plants, *Plasmopara viticola* in grapes, Alternaria species in fruit and vegetables. The compounds of formula I may also be used for protecting materials (e.g. preservation of timber against *Paecilomyces variotii*).

Pharmaceutical Compositions. While it is possible that, for use in therapy, compounds of the invention may be administered as the raw chemical, it is preferable to present the active ingredient in a pharmaceutical composition. The invention thus further provides a pharmaceutical composition comprising a compound of formula (I) or a pharmaceutically acceptable salt thereof, together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, rectal, topical, ophthalmic or genito-urinary administration or in a form suitable for administration by inhalation or insufflation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate or crosscarmellose sodium; or wetting agents such as sodium lauryl sulphate. The tablets which include chewable, dispersible or effervescent tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilizing and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form of an aerosol spray presentation from pressurized packs with the use of a suitable propellant, e.g. dichlorodifluoromethane, trichlorofluoromethane, dichlorotetrafluoroethane, carbon dioxide or other suitable gas, or from a nebuliser. In the case of a pressurized aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch or as a modified physical form of the drug substance alone. The powder composition may be presented in unit dosage form in, for example, capsules or cartridges of e.g. gelatin, or blister packs from which the powder may be administered with the aid of an inhaler or insufflator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilized components. Pour-ons may, for example, be formulated for veterinary use in oils containing organic solvents, optionally with formulatory agents, e.g. stabilizing and solubilizing agents. Pessaries and tampons for vaginal insertion may be formulated using conventional techniques and, where appropriate, may contain an effervescent vehicle. Such compositions may also contain other active ingredients such as corticosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilizing, dispersing and or flavouring agents.

Transdermal administration may be affected by the design of a suitable system which promotes absorption of the active compound through the skin and would typically consist of a base formulation enclosed within an adhesive stick-on patch comprising backing films, membranes and release liners. Such systems may include absorption enhancers such as alcohols or work by promoting ionotophoresis.

The composition according to the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.001 mg to 1000 mg, advantageously 0.01 mg to 400 mg, of active ingredient where a compound of the invention is to be administered orally. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary number of days.

Compounds of the invention may also be used in combination with other therapeutic agents, and the invention thus provides, in a further aspect, a combination comprising a compound of the invention together with another therapeutically active agent.

Thus, for example the compounds of the invention may be used in combination with one or more other antifungal agents, such as a polyenic derivative e.g. (Amphotericin B, Nystatin, a lipid formulation of Amphotericin B) an azole derivative e.g. (Fluconazole, Intraconazole, Ketoconazole, Miconazole, Clotrimazole, ZD-08070, UK-109496, SCH 56592), 5-Fluorocytosine, a Pneumocandin or Echinocandin derivative such as Cilofungin, LY-303366, L-733560, L-743872 or other cell wall active compound such as Nikkomycin Z and/or one or more immunomodulating agents such as an interferon e.g. (IFN-), interleukine e.g. (IL-1, IL-2, IL-3 and IL-8) and colony stimulating factors, [(G)-CSF, (M)-CSF and (GM)-CSF] and defensines. Particularly advantageous compounds for use with compounds of the invention include Intraconazole, Flucytosine, Fluconazole or Amphotericin B.

When the compounds of the invention are administered in combination with another antifungal agent the compounds of the invention and the other fungal agent can be administered at the recommended maximum clinical dosage or at lower doses.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations When a compound of the invention is used in combination with a second therapeutic agent against the same condition the dose of each compound may differ from that when the compound is used alone. Appropriate doses will be readily appreciated by those skilled in the art.

Agrochemical Compositions. The compounds of formula I can be used in either an unmodified form or preferably together with adjuvants conventionally employed in the art of agrochemical formulation and are for this purpose forms known mainly as: emulsifiable concentrates, coatable pastes, directly sprayable or dilutable solutions, dilute solution, suspensions (including high-percentage aqueous, oily or other suspensions), dispersions, oil dispersions, broadcasting agents, wettable powders, soluble powders, dusts, granules, and encapsulations. The formulations are prepared in known manner, e.g. by homogeneously mixing and/or grinding the active ingredients with extenders, e.g. solvents, solid carriers and, where appropriate, surface-active compounds (surfactants). Powders, dusts and broadcasting agents may be prepared by mixing or grinding the active ingredients with a solid carrier. Granules, e.g., coated, impregnated or homogeneous granules, may be prepared by bonding the active ingredients to solid carriers.

Suitable solvents are: aromatic hydrocarbons, preferably the fractions containing 8 to 12 carbon atoms, such as xylene mixtures or substituted naphthalenes, chlorinated aromatics such as chlorobenzenes, phthalates, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones such as cyclohexanone, amines such as ethanolamine, strongly polar solvents, such as N-methyl-2-pyrrolidone, dimethyl sulfoxide or dimethylformamide, and vegetable oils or epoxidised vegetable oils, such as epoxidised coconut oil or soybean oil; and water.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formnaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Examples of solid carriers are mineral earths such as silicic acids, silica gels, silicates, talc, kaolin, attapulgus clay, limestone, lime, chalk, bole, loess, clay, dolomite, diatomaceous earth, aluminas calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Compounds of formula I may be mixed and applied together with other active ingredients, for example herbicides, insecticides, bactericides, nematocides, molluscicides, growth regulators, micronutrients, and fertilizers. The other ingredients may also be one or more fungicides belonging to but not restricted to the following classes of fungicides: carboxamides, benzimidazoles, triazoles, hydroxypyridines, dicarboxamides, phenylamides, thiadiazoles. carbamates, cyano-oximes, cinnamic acid derivatives, morpholines, imidazoles, B-methoxy acrylates and pyridines/pyrimidines. Furthermore, these additional active ingredients may be used as mixtures of several of the preparations, if desired together with other application promoting adjuvants usually used in the art of formulation.

Suitable carriers and adjuvants can be solid or liquid and correspond to the substances typically used in formulation technology (e.g. natural or regenerated mineral substances, solvents, disperants, and wetting agents).

The following list of fungicides with which compounds of formula I may be combined is intended to illustrate possible combinations but not to impose any restrictions. Examples of fungicides which may be combined with compounds of formula I are: sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc N,N'-ethylenebisdithiocarbamate, ammonia complex of zinc N,N'-propylenebisdithiocarbamate, zinc N,N'-propylenebisdithiocarbamate and N,N'-polypropylenebis(thiocarbamyl) disulfide; nitro derivative, such as dinitro(1-methylheptyl)-phenyl crotonate, 2-sec-butyl-4,6-dinitrophenyl 3,3-dimethylacrylate,2-sec-butyl-4,6-dinitrophenyl isopropylcarbonate and diisopropyl 5-nitroisophthalate; heterocyclic substances, such as 2-heptadecylimidazol-2-yl acetate, 2,4-dichloro-6-(o-chloroanilino)-s-triazine, O,O-diethyl phthalimidophosphonothioate, 5-amino-1-[bis-(dimethylamino)-phosphinyl]-3-phenyl-1,2,4-triazole, 2,3-dicyano-1,4-dithioanthraquinone, 2-thio-1,3-dithio[4,5-b]quinoxaline, methyl 1-(butylcarbamyl)-2-benzimidazolecarbamate, 2-methoxycarbonylaminobenzimidazole, 2-(fur-2-yl)-benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric acid diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline and its copper salt, 2,3-dihydro-5-carboxanilido-6-methyl-1,4-oxathiyne, 2,3-dihydro-5-carboxanilido-6-methyl-1,4-oxathiyne 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethyl-N-cyclohexylfuran-3-carboxamide, N-cyclohexyl-N-methoxy-2,5-diethylfuran-3-carboxamide, 2-methylbenzanilide, 2-iodobenzanilide, N-formyl-N-morpholine-2,2,2-trichloroethylacetal, piperazine-1,4-diylbis-(1-(2,2,2-trichloroethyl)-formamide), 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N[3-(p-tert.-butylphenyl)-2-methylpropyl]-cis-2,6-dimethylmorpholine, N-3-(p-tert.-butylphenyl)-2-methylpropyl]-piperidine, 1-2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N]-imidazolylurea, 1-(4-chlorophenoxy)-3,3-dimethyl-1-(1H-1,2,4-triazol-1-yl)-butan-2-one, 1-(4-chlorophenoxy)-3,3-dimethyl-1-(1H-1,2,4-triazol-1-yl)-butan-2-ol, alpha -(2-chlorophenyl)-alpha-(4-chlorophenyl)-5-pyrimidinemethanol, 5-butyl-(2-dimethylamino-4-hydroxy-6-methylpyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene, and various fungicides, such as dodecylguanidine acetate, 3-[3-(3,5-dimethyl-2-oxycyclohexyl)-2-hydroxyethyl]-glutaramide, hexachlorobenzene, DL-methyl-N-(2,6-dimethylphehyl)-N-fur-2-yl alanate, methyl DL-N-(2,6-dimethylphenyl)-N-(2]-methoxyacetyl)-alanate, N-(2,6-dimethylphenyl)-N-chloroacetyl-DL-2-aminobutyrolactone, methyl DL-N-(2,6-dimethylphenyl)-N-(phenylacetyl)-alanate, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-(3,5-dichlorophenyl)-1-isopropylcarbamylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)-pentyl]-1H-1,2,4-triazole, 2,4-difluoro-a-(1H-1,2,4-triazol-1-ylmethyl)-benzhydryl alcohol, N-(3-chloro-2,6-dinitro-4-trifluoromethylphenyl)-5-trifluoromethyl-3-chloro-2-aminopyridine, and 1-((bis-(4-fluorophenyl)-methylsilyl)-methyl)-1H-1,2,4-triazole.

As with the nature of compositions, the method of application such as spraying, atomizing, dusting, scattering, coating, dressing, and pouring are chosen in accordance with the intended objectives of the application and the prevailing circumstances. One method of applying the active ingredient or agrochemical composition containing at least one of the stated compounds is application to the plants (i.e. foliar application). However, the active ingredient can also penetrate the plant through the roots via the soil (i.e. soil application). This may be in the form of either a liquid application to the soil (drench) or a granular application.

The active ingredient can also be applied to plant propagation material such as seeds (fruits, tubers or grains) or plant cuttings, in either liquid form (coating) or in solid form (dressing). Seeds, for example, can be dressed before sowing. The compounds of the invention can also be applied to grains either by impregnating the grains with a liquid formulation of by coating them with a solid formulation. The composition can also be applied to the locus of planting when planting the propagation material, for example to the seed furrow during sowing.

Advantageous rates of application are normally from 10 g to 50 kg of active ingredient (a.i.) per hectare, preferably 100 g to 2 kg a.i./ha, most preferably 100 g to 600 g a.i./ha. The active ingredients of the stated compounds are typically used in the form of compositions and can be applied to the plant, or to parts of the plant either simultaneously or in succession with further active ingredients. These further active ingredients can be fertilizers, additional micronutrients, or other plant growth affecting compounds. They can, however, also be selective herbicides, insecticides, bactericides, nematocides, insecticides, and molluscicides, as well as other fungicides.

PREPARATION OF STARTING MATERIAL

Fermentation Production of Sordarin

The following media are used in the fermentation of *Rosellinia subiculata* (ATCC 74386) and ATCC 74387 in the production of sordarin.

SEED MEDIUM 1

| Component | g/L |
|---|---|
| Yeast extract | 4.0 |
| Malt extract | 8.0 |
| Glucose | 4.0 |
| Junlon | 1.5 |

The medium was prepared with distilled water, the pH adjusted to 7.0 prior to sterilization, and was dispensed at 50 ml/250 ml unbaffled Erlenmeyer flask. Cotton closures were used. Sterilization was at 121° C. for 20 minutes.

SEED MEDIUM 2

| Component | (g/L) | Trace elements solution Component | (g/l) |
|---|---|---|---|
| Corn steep liquor (dried) | 2.5 | $FeSO_4 \cdot 7H_2O$ | 1.0 |
| Tomato paste | 40.0 | $MnSO_4 \cdot 4H_2O$ | 1.0 |
| Oat flour | 10.0 | $CuCl_2 \cdot 2H_2O$ | 0.025 |
| Glucose | 10.0 | $CaCl_2 \cdot H_2O$ | 0.1 |
| Trace elements solution | 10.0 ml/L | $H_3BO_3$ | 0.056 |
| | | $(NH_4)_6MoO_{24} \cdot 4H_2O$ | 0.019 |
| | | $ZnSO_4 \cdot 7H_2O$ | 0.2 |

Trace elememts prepared in 0.6N HCl

The medium was prepared with distilled water, the pH adjusted to 6.8 prior to sterilization, and was dispensed at 50 ml/250 ml unbaffled Erlenmeyer flask. Cotton closures were used. Sterilization was at 121° C. for 20 minutes.

Solid Production Medium 1

1. Solid portion:

Add 675 cc vermiculite to a 2-liter roller bottle. Plug with latex closure; autoclave for 60 min., plus 30 min. dry.

2. Liquid portion:

To a 500 ml bottle, add 220 ml of the following:

| Component | g/L |
|---|---|
| Glucose | 150.0 |
| Glycerol | 20.0 |
| Yeast extract | 4.0 |
| $NaNO_3$ | 1.0 |
| Monosodium Glutamate | 3.0 |
| $Na_2HPO_4$ | 0.5 |
| $MgSO_4 \cdot 7H_2O$ | 1.0 |
| K-elements | 1.0 ml/L |
| $CaCO_3$ | 8.0 |
| K-elements | |
| $FeCl_3 \cdot 6H_2O$ | 5.8 |
| $MnSO_4 \cdot H_2O$ | 0.1 |
| $CoCl_2 \cdot 6H_2O$ | 0.02 |
| $CuSO_4 \cdot 5H_2O$ | 0.015 |
| $Na_2MoO_4 \cdot 2H_2O$ | 0.012 |
| $ZnCl_2$ | 0.02 |
| $SnCl_2 \cdot 2H_2O$ | 0.005 |
| $H_3BO_3$ | 0.01 |
| KCl | 0.02 |
| HCl (concentrated) | 2.0 ml/L |

The medium was prepared with distilled water, pH to 7.0 prior to sterilization. Glucose was autoclaved separately. It was dispensed in 500 ml bottles and autoclaved at 121° C. for 15 minutes.

Liquid Production Medium 1

| Component | g/L |
|---|---|
| Glycerol | 75.0 |
| Glucose | 75.0 |
| Tomato paste | 5.0 |
| NZ amine Type A | 4.0 |
| Ardamine PH | 5.0 |
| $K_2HPO_4$ | 0.5 |
| $MgSO_4 \cdot 7H_2O$ | 0.25 |
| KCl | 0.25 |

-continued

| Liquid Production Medium 1 | |
|---|---|
| Component | g/L |
| ZnSO$_4$ · 7H$_2$O | 0.5 |
| CaCO$_3$ | 10.0 |

The medium was prepared with distilled water, pH to 7.0 prior to sterilization. The medium was dispensed at 50 ml per 250 ml unbaffled Erlenmeyer flask. The flasks were closed with cotton and autoclaved at 121° C. for 20 minutes.

Solid Production Medium 2

1. Solid portion:
Add 675 cc vermiculite to a 2-liter roller bottle. Plug with latex closure; autoclave for 60 min., plus 30 min. dry.

2. Liquid portion:
To a 500 ml bottle, add 220 ml of the following:

| Component | g/L |
|---|---|
| Sucrose | 60.0 |
| Glucose | 80.0 |
| Glycerol | 60.0 |
| Citric Acid | 15.0 |
| NZ amine Type A | 5.0 |
| NaNO$_3$ | 1.0 |
| KH$_2$PO$_4$ | 0.5 |
| MgSO$_4$ · 7H2O | 0.5 |
| CaCO$_3$ | 0.5 |
| K-elements | 1 ml/L |
| K-elements | |
| FeCl$_3$ · 6H$_2$O | 5.8 |
| MnSO$_4$ · H$_2$O | 0.1 |
| CoCl$_2$ · 6H$_2$O | 0.02 |
| CuSO$_4$ · 5H$_2$O | 0.015 |
| Na$_2$MoO$_4$ · 2H2O | 0.012 |
| ZnCl$_2$ | 0.02 |
| SnCl$_2$ · 2H$_2$O | 0.005 |
| H$_3$BO$_3$ | 0.01 |
| KCl | 0.02 |
| HCl (concentrated) | 2.0 ml/L |

The medium was prepared with distilled water, pH to 7.0 prior to sterilization. It was dispensed at 220 ml per 500 ml bottle and autoclaved at 121° C. for 15 minutes.

Liquid Production Medium 2

The composition is the same as the liquid portion of Solid Production Medium 1. The medium was prepared with distilled water, pH to 7.0 prior to sterilization. Glucose was autoclaved separately. The medium was dispensed at 50 ml per 250 ml unbaffled Erlenmeyer flask. The flasks were closed with cotton and autoclaved at 121 ° C. for 15 minutes.

Production of Sordarin by Fermentation of *Rosellina subiculata* (MF6239, ATCC 74386)

1. CULTURE: A portion of the agar slant containing the culture was aseptically transferred to seed medium 1 (50 ml /250 ml unbaffled flask). This was incubated on a 2-inch throw gyratory shaker, 220 rpm for 5 days at 25° C., 85% relative humidity (rh), to obtain biomass. Portions of the biomass were transferred into sterile vials containing glycerol and frozen (as frozen vegetative mycelia (FVM)). These were maintained in a final concentration of 10–15% glycerol at −75° C. Secondary FVMs were prepared from a primary FVM by transferring 1.0 ml of the thawed primary FVM into seed medium 2, incubating 7 days, 25° C., 220 rpm and freezing as above.

2. SEED: A frozen vial (FVM) of MF6239 was thawed to room temperature and used to inoculate seed cultures with 1.0 ml per 50 ml seed medium 2. These were grown on a gyratory shaker (220 rpm) for 7 days at 25° C., 85% rh.

3. PRODUCTION: On solid production medium. An aliquot (10–12 ml) of the seed was placed into 220 ml of the liquid portion of solid production medium 1. This flask was swirled vigorously to disperse the biomass. The contents were dispensed by pouring into a 2 L roller culture vessel which contained 675 cubic centimeters of large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22° C., 70% rh for 17 days, to obtain a secondary metabolite in the fermentation medium.

In liquid production medium. Seed cultures were inoculated as described above. An aliquot of the seed (1.5 ml) was used to inoculate each production flask, containing 50 ml/250 ml flask of liquid production medium 1. Flasks were incubated on a gyratory shaker (220 rpm) for 7–21 days at 25° C., 50–85% rh.

Production of Sordarin by Fermentation of MF6232 (ATCC 74387)

1. CULTURE: A portion of the agar slant containing MF6232 was aseptically transferred to seed medium 1 (50 ml /250 ml unbaffled flask). This was incubated on a 2-inch throw gyratory shaker, 220 rpm for 3 days at 25° C., 85% relative humidity (rh), to obtain biomass. Portions of the biomass were transferred into sterile vials containing glycerol and frozen (as FVM). These were maintained in a final concentration of 10–15% glycerol at −75° C. Secondary FVMs were prepared from a primary FVM by transferring 1.0 ml of the thawed primary FVM into seed medium 2 (composition below), incubating 7 days, 25° C., 220 rpm, and freezing as above.

2. SEED: A frozen vial (FVM) of MF6232 was thawed to room temperature and used to inoculate seed cultures with 1.0 ml per 50 ml seed medium 2. These were grown on a gyratory shaker (220 rpm) for 7 days at 25° C., 85% rh.

3. PRODUCTION: On solid production medium. An aliquot (10–12 ml) of the seed was placed into 220 ml of solid production medium 2. This was swirled vigorously to disperse the biomass. The contents were dispensed by pouring into a 2 L roller culture vessel which contained 675 cubic centimeters of large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22° C., 70% rh for 21 days, to obtain a secondary metabolite in the fermentation medium.

In liquid production medium. Seed cultures were inoculated as described above. An aliquot of the seed (1.5 ml) was used to inoculate each production flask, containing 50 ml/250 ml flask of liquid production medium 2. Flasks were incubated on a gyratory shaker (220 rpm) for 7–21 days at 25° C., 50–85% rh.

Large Scale Production of Sordarin by MF6232 (ATCC 74387)

The liquid portion of solid production medium 1 was used for both the seed and production fermenters. Cerelose, added post-sterilely, in the seed fermenter medium was 30 g/L while that of the production fermenter medium was 150 g/L. Seed fermenters were inoculated with 2 L of culture grown in shaker flasks. These fermenters were permitted to grow at 25° C. for 30 hours until the oxygen uptake rate was about 3 mmol/L-hr. At 30 hours, 25 L of fermenter seed culture was transferred to the production fermenter.

Growth in the production fermenter reached 8–10 mmol/L-hr after 50 hours and declined to between 5–7 by the end of the cultivation. Dissolved oxygen was controlled by increasing agitation. Broth pH was not controlled and generally decreased to 5.3 at 200 hours. The temperature was 25° C.

After 280 hours of growth the fermentation was terminated and the preparations for harvest begun. The pH was adjusted to about 12 with sodium hydroxide and the batch aged for 20 hours at fermentation temperature. The pH was then adjusted to 6.0 with sulfuric acid prior to transfer into drums for further processing.

Isolation of Sordarin

ISOLATION I

A methyl ethyl ketone extract of the fermentation of culture MF6232 (ATCC 74387) corresponding to 64 mL of whole broth was concentrated to dryness in vacuo (365 mg). This material was dissolved in 2 parts methanol in 98 parts methylene chloride to a final volume of 4.6 ml. A 4.3 ml portion (341 mg) was applied to a 60 ml silica gel 60 (0.040–0.0630 mm, 230–400 mesh, E. Merck) flash chromatography column equilibrated with 2 percent methanol in methylene chloride. The column was eluted by a step gradient of 240 ml each of 2, 5, 10, and 30 percent methanol in methylene chloride followed by 120 ml of methanol. Sixteen 15 ml fractions were collected from each solvent system. The product rich fractions 39–56 were determined by biological assay.

The crude fraction pool was concentrated to dryness in vacuo (103.1 mg). A 34.4 mg portion of this sample was further purified by HPLC separation (Zorbax Rx-$C_8$, 5 μm, 9.4 mm×250 mm, eluted with mobile phase consisting of 20% acetonitrile/80% aqueous 0.01 M $K_2HPO_4$ adjusted to pH 6.9 with concentrated $H_3PO_4$, flow rate 4 ml/min. at 40° C., diode array detection). Four milliliter fractions were collected. The product rich fractions 16–20 were pooled and concentrated in vacuo to approximately twenty-five percent of the original volume. The concentrate was doubly extracted with an equal volume of ethyl acetate and the ethyl acetate layers were washed with an equal volume of brine, dried over anhydrous $Na_2SO_4$ and concentrated in vacuo to yield 3.7 mg of sordarin.

ISOLATION II

A methyl ethyl ketone extract of the batch -004Y fermentation of culture MF6232 (ATCC$_{74387}$) corresponding to 980 mL of whole broth was concentrated to dryness in vacuo (4.9 g). This material was dissolved in 1 part methanol in 9 parts methylene chloride to a final volume of 21.5 ml. A 21 ml portion (4.8 g) was applied to a 500 milliliter silica gel 60 (0.040–0.0630 mm, 230–400 mesh, E. Merck) chromatography column equilibrated with 2 percent methanol in methylene chloride. The column was eluted at a flowrate of 25 ml/min. by a step gradient beginning with 1 liter each of 2 and 5 percent methanol in methylene chloride followed by 2 liters of 15 percent methanol. The column elution was completed with 1 liter each of 30 and 100 percent methanol. Twenty-five milliliter fractions were collected. Product rich fractions 75–85 and 111–121 were determined by biological assay and contained Compound I by RP HPLC analysis under acidic conditions.

The crude fraction pools, 75–85 and 111–121 were concentrated, separately, to dryness in vacuo (69.3 mg and 95.3 mg, respectively). Two 34 mg portions of pool 75–85 were further purified by two identical HPLC separations (Zorbax Rx-C8, 7 μm, 21.2 mm×250 mm, eluted with mobile phase consisting of 40% acetonitrile/60% $H_2O$ with 0.1% $H_3PO_4$ overall, flow rate 20 ml/min. at 25° C., 220 nm). Ten milliliter fractions were collected. The product rich fractions 27–31 from both runs were pooled together and concentrated in vacuo to approximately forty percent of the original volume. The concentrate was extracted with an equal volume of ethyl acetate and washed with an equal volume of brine, dried over anhydrous $Na_2SO_4$ and concentrated in vacuo to yield 27 mg of sordarin. Two 46 mg portions of pool 111–121 were also further purified under the identical HPLC conditions listed above. Fractions 25–28 from both runs were combined and prepared as described above to yield an additional 17 mg of sordarin.

INTERMEDIATE 1

[1R-(1α,3aβ,4β,4aβ,7β,7aα,8aβ)] Benzyl 4-formyl-8a-(hydroxymethyl)-4,4a,5,6,7,7a,8,8a-octahydro-7-methyl-3-(1-methylethyl)-1,4-methano-s-indacene-3a(1H)-carboxylate (sordaricin benzyl ester)

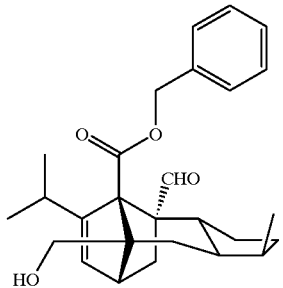

Sordarin (2 mg) was dissolved in 1 mL of acetone. Concentrated HCl (0.2 mL) was added. The mixture was stirred at room temperature for 1 day. After dilution with water and aqueous work-up ($CH_2Cl_2$), the organic fraction was dried over $Na_2SO_4$, filtered and concentrated in vacuo. The mixture was dissolved in 2 mL of DMF to which was added 0.1 mL of benzyl bromide, followed by excess solid $NaHCO_3$. The mixture was stirred at room temperature overnight, and was then concentrated in vacuo. Chloroform was added to the mixture which was filtered to remove the $NaHCO_3$. The filtrate was concentrated in vacuo and purified by preparative thin layer chromatogrpahy (PTLC) to yield 1.0 mg of sordaricin benzyl ester. $^1H$ NMR ($CDCl_3$): δ0.51 (3H, d, J=6.9), 0.82 (3H, d, J=6.6), 0.91 (1H, m), 1.0 (3H, d, J=6.6), 1.18 (1H, d, J=12.6), 1.50–2.00 (9H, m), 2.24 (1H, m), 2.51 (1H, m), 3.48 (1H, d, J=11.0), 3.87 (1H, d, J=11.0), 5.11 (1H, d, J=11.7), 5.31 (1H, d,J=11.7), 6.04 (1H, d, J=2.1), 7.31–7.40 (5H, m), 9.62 (1H, s).

INTERMEDIATE 2

[1R-(1α,3aβ,4β,4aβ,7β,7aα,8aβ)] 4-Methoxybenzyl 4-formyl-8a-(hydroxymethyl)-4,4a,5,6,7,7a,8,8a-octahydro-7-methyl-3-(1-methylethyl)-1,4-methano-s-indacene-3a(1H)-carboxylate (sordaricin p-methoxybenzyl ester)

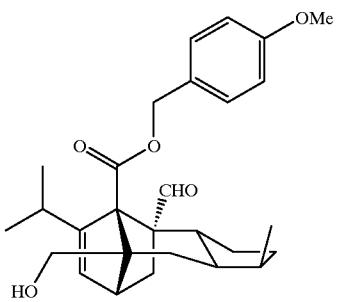

The same procedure for the preparation of sordaricin benzyl ester was followed, with the use of 4-methoxybenzyl chloride instead of benzyl bromide. $^1$H NMR (CDCl$_3$): δ0.51 (3H, d, J=6.9), 0.82 (3H, d, J=6.9), 1.00 (3H, d, J=6.9), 0.90–2.00 (11H, m), 2.23 (1H, m), 2.49 (1H, t, J=3.8), 3.79 (3H, s), 4.61 (2H, s), 5.05 (1H, d, J=11.7), 5.26 (1H, d, J=11.7), 6.03 (1H, d, J=3.2), 6.88 (2H, d, J=8.7), 7.28 (2H, d, J=8.7), 9.60 (1H, s).

INTERMEDIATE 3
[1R-(1α,3a,4β,4aβ,7β,7aα,8aβ)] Allyl 4-formyl-8a-(hydroxymethyl)-4,4a,5,6,7,7a,8,8a-octahydro-7-methyl-3-(1-methylethyl)-1,4-methano-s-indacene-3a(1H)-carboxylate (sordaricin allyl ester)

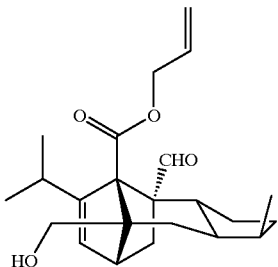

A similar procedure for the preparation of sordaricin benzyl ester is followed, with the use of allyl bromide instead of benzyl bromide. In this manner, the title compound is obtained.

INTERMEDIATE 4
[1R-(1α,3aβ,4β,4aβ,7β,7aα,8aβ)] 4-formyl-8a-(hydroxymethyl)-4,4a,5,6,7,7a,8,8a-octahydro-7-methyl-3-(1-methylethyl)-1,4-methano-s-indacene-3a(1H)-carboxylic acid (sordaricin)

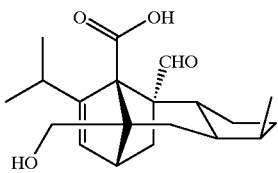

To a MeOH solution of sordaricin benzyl ester (0.6 mg) was added Pearlman's catalyst. The mixture was stirred under hydrogen (balloon pressure) for 15 minutes. After filtration through cotton wool and concentration in vacuo, 0.4 mg of sodaricin was obtained. $^1$H NMR (CDCl$_3$): δ0.82 (3H, d, J=6.8), 0.98 (3H, d, J=6.6), 1.01 (3H, d, J=6.9), 1,23 (1H, m), 1.25 (1H, d, J=12.6), 1.58–2.10 (9H, m), 2.34 (1H, m), 2.41 (1H, t, J=3.6), 3.45 (1H, d, J=11.0), 4.14 (1H, d, J=11.0), 6.05 (1H, d, J=3.0), 9.75 (1H, s).

INTERMEDIATE 5

[1R-(1α,3aβ,4β,4aβ,7β,7aα,8aβ)] Benzyl 4-cyano-8a-(hydroxymethyl)-4,4a,5,6,7,7a,8,8a-octahydro-7-methyl-3-(1-methylethyl)-1,4-methano-s-indacene-3a(1H)-carboxylate

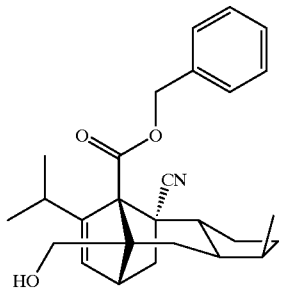

Sordaricin benzyl ester (161.2 mg) was dissolved in 6 mL of N,N-dimethylformamide and p-methoxybenzyl chloride (1 mL) was added followed by excess sodium hydride (50 mg of a 60% dispersion in mineral oil). The mixture was stirred overnight. The mixture was diluted with ether and carefully washed with water. The ether layer was dried over anhydrous sodium sulfate and the volatiles removed in vacuo. The residue was purified by silica gel chromatography to give 192.5 mg (93%) of the p-methoxybenzyl ether.

The ether obtained above (150 mg) was dissolved in 5 mL of dry ethanol and 3 mL of dry pyridine was added. Hydroxylamine hydrochloride (96 mg) was added and the mixture was heated to 70° C. for 3 hours. The reaction mixture was cooled and concentrated in vacuo. The residue was dissolved in ether, washed with water and dried over anhydrous sodium sulfate. The residue, obtained after removal of the ether in vacuo, was purified by PTLC to give 143.4 mg of the aldoxime (93%).

The oxime (143 mg) was dissolved in 5 mL of toluene to which excess (methoxycarbonylsulfamoyl)-triethylammonium hydroxide inner salt (700 mg) was added. The mixture was stirred at 70° C. for 2 hours. After concentration in vacuo, the residue was purified by PTLC to give 116.6 mg of the nitrile (84%).

The nitrile from above (67.5 mg) was dissolved in 5 mL of dichloromethane to which DDQ (43 mg) and 0.5 mL of water were added. The mixture was stirred at room temperature for 2 hours. After aqueous work-up and purification by PTLC, 47.6 mg (91%) of the title compound was obtained.

The following examples are provided to more fully illustrate the invention, and are not to be construed as limiting the scope of the invention in any manner.

EXAMPLE 1

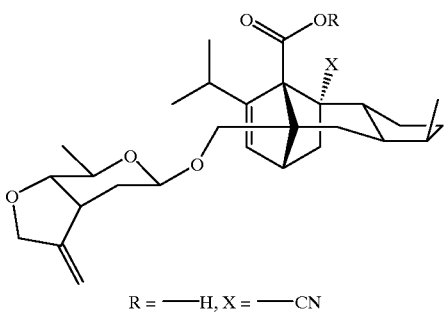

R = ——H, X = ——CN

Part A. The compound (1 equivalent) described by the above formula but where R=—CH(C$_6$H$_5$)$_2$ and X=—CHO and whose preparation is described in WO 96/14326 is dissolved in ethanol and an equal volume of pyridine is added followed by hydroxylamine hydrochloride (10 equivalents). The reaction mixture is stirred under a nitrogen atmosphere for approximately 20 minutes or until sufficient reaction has taken place as judged by analytical TLC. The mixture is concentrated under reduced pressure and partitioned between water and dichloromethane. The organic phase is dried over anhydrous sodium sulfate, filtered and concentrated in vacuo. The residue is purified by PTLC (hexane:ethyl acetate) to give the product.

Part B. The product from Part A (1 equivalent) is dissolved in toluene and Burgess' Salt (5 equivalents) is added. The mixture is stirred under nitrogen at 60° C. for about 1 hour or until a sufficient amount of starting material has reacted. The reaction mixture is cooled and the volatiles removed in vacuo. Purification by PTLC (hexane:ethyl acetate) gives the product.

Part C. The product from Part B is dissolved in 2% trifluoroacetic acid in dichloromethane (w/w) at 0° C. and is stirred for about 4 hours or until sufficient reaction has taken place. The volatiles are removed under reduced pressure and the product purified by PTLC to give the title compound.

EXAMPLE 2

[1R-(1α,3aβ,4β,4aβ,7β,7aα,8aβ)] 8a-[(6-deoxy-4-O-methyl-β-D-altropyranosyloxy)methyl]-4-cyano-4,4a,5,6,7,7a,8,8a-octahydro-7-methyl-3-(1-methylethyl)-1,4-methano-s-indacene-3a(1H)-carboxylic acid (4-cyano-4-deformylsordarin)

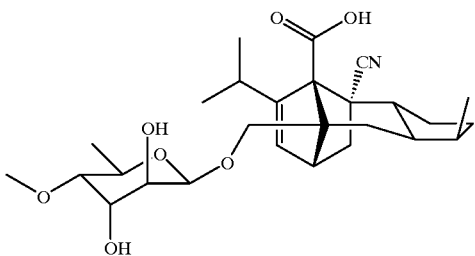

Sordarin (50 mg) was dissolved in 3 mL of N,N-dimethylformamide and 0.3 mL of benzyl bromide was added followed by 200 mg of sodium hydride (60% dispersion in mineral oil). The mixture was stirred overnight at room temperature. After aqueous workup (diethyl ether) and purification by PTLC, 2',3'-di-O-benzylsordarin benzyl ester was obtained.

A solution of 2',3'-di-O-benzylsordarin benzyl ester (1 equivalent) from above was prepared in ethanol/pyridine (2:1). Excess hydroxylamine hydrochloride was added to the mixture and it was heated to 70° C. with stirring for 2 hours. The mixture was concentrated in vacuo an aqueous workup (dichloromethane) was performed. Purification by PTLC gave 2',3'-di-O-benzyl-4-aldoximesordarin benzyl ester.

To a solution of 2',3'-di-O-benzyl-4-aldoximesordarin benzyl ester from above in toluene was added an excess of (methoxycarbonylsulfamoyl)-triethylammonium hydroxide inner salt (Burgess' Reagent). The mixture was stirred under a nitrogen atmosphere at 70° C. for 2 hours. After concentration in vacuo and purification by PTLC, 2',3'-di-O-benzyl-4-cyano-4-deformylsordarin benzyl ester was obtained.

A solution of the benzyl ester from above was prepared in methanol. Palladium hydroxide on carbon (Pearlman's catalyst) was added and the vessel was flushed with hydrogen gas. The mixture was stirred vigorously under one atmosphere of hydrogen for 15 minutes. The mixture was filtered and the solution concentrated in vacuo to give the title compound. MS (CI): m/z=507.5 (M+NH$_4$)$^+$

EXAMPLE 3

[1R-(1α,3aβ,4β,4aβ,7β,7aα,8aβ)] 8a-[(6-deoxy-β-D-altropyranosyloxy)methyl]-4-cyano-4,4a,5,6,7,7a,8,8a-octahydro-7-methyl-3-(1-methylethyl)-1,4-methano-s-indacene-3a(1H)-carboxylic acid (4-cyano-4-deformyl-4'-demethyl sordarin)

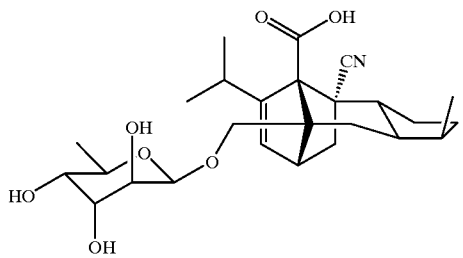

One mL of frozen mycelium of *Streptomyces avermitilis* MA 4848 (ATCC 31272) is inoculated into each of 8 baffled Erlenmeyer flasks containing 40 ml BaSa medium [per liter: 20 g Yeast Extract (Difco), 20 g Hycase (salt-free, Sheffield), 20 g dextrose, 2 g KNO3, 10 ml trace elements (as defined below). pH 7.0, autoclaved 20 min]. Flasks are incubated 24 h at 27° C. at 220 rpm. The pH is 6.7–6.8. Mycelia are examined microscopically for non-mycelial contaminants.

| Trace elements | 1 liter |
| --- | --- |
| NaCl (12.5% soln) | 4 ml |
| MgSO$_4$ · 7H$_2$O (12.5% soln) | 4 ml |
| FeSO$_4$ · 7H$_2$O | 25 mg |
| MnSO$_4$ · H$_2$O (0.5% soln) | 1 ml |
| ZnSO$_4$ · 7H$_2$O (1% soln) | 1 ml |
| CaCl$_2$ · 2H$_2$O (2% soln) | 1 ml |

Forty mg of the title compound from Example 2 (4-cyano-4-deformylsordarin) is dissolved in 0.40 ml 80% ethanol and 50 μl added to eack flask. The mixture is incubated for 18 h at 27° C. Conversion is complete as determined by analytical HPLC. The broth (200 mL) is diluted with an equal volume of methanol (200 mL) for extraction and the solids removed by centrifugation. The supernatant is concentrated in vacuo to remove most of the methanol and the remaining solution (~200 mL) is adjusted to pH 11 with NaOH. This solution is extracted twice with dichloromethane (200 mL). The aqueous layer is adjusted to pH 2.5 with dilute sulfuric acid and extracted twice with dichloromethane. The combined dichloromethane layers are washed with water, brine and dried over anhydrous sodium sulfate. The sodium sulfate is removed by filtration and the dichloromethane removed in vacuo to yield a solid (53 mg). The residue is purified using preparative RP HPLC on Phenomenex Primesphere C8 (5μ, 9.4×250 mm). A mobile phase consisting of acetonitrile:water (34:66) containing 0.1% phosphoric acid is used at a flow rate of 3.5 mL/min. at 40° C. The title compound elutes at 14.4 minutes. The rich cut fractions are combined and the acetonitrile removed under a stream of $N_2$. The remaining aqueous solution is extracted with dichloromethane as described above to yield 7.2 mg of the title compound.

$^1$H NMR (1.5 mg in 0.125 mL $CD_3OD$): δ0.790 (d, 6.8, 3H), 1.059 (d, 6.8, 3H), 1.161 (d, 6.8, 3H), 1.14–1.32 (m), 1.257 (d, 6.4, 3H), 1.650 (m, 1H), 1.74–1.86 (m), 2.00–2.18 (m), 2.432 (dd, 4.4, 12.8, 1H), 2.670 (br heptet, 6.8, 1H), 2.836 (brdd, 3.6, 1H), 3.450 (dd, 4.0, 9.2, 1H), 3.67 (m, 2H), 3.721 (d, 9.6, 1H), 3.871 (dd, 3.6, 3.6, 1H), 3.914 (d, 9.6, 1H), 4.572 (brs), 6.225 (brd, 3.2). IR (thin film on ZnSe): 2958, 2234, 1713, 1071 cm$^{-1}$. MS: 475.2607 (M+)

EXAMPLE 4

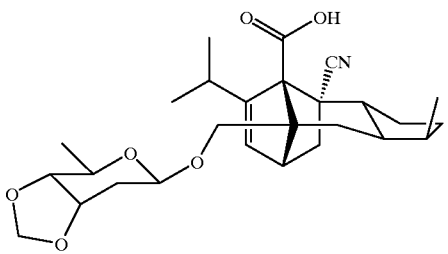

Part A. Digitoxose (0.500 g, 3.37 mmol) was placed in a flask and azeotroped with dry benzene. The material was dissoved in 5 mL of dry pyridine and 5 mL of acetic anhydride was added. The reaction mixture was stirred for 18 hours. Thin layer chromatographic analysis (Silica gel, ethyl acetate/hexanes 1:2) showed the complete dissapearance of digitoxose. The volatiles were removed in vacuo to give 1.013 g of a pale yellow oil. $^1$H NMR (CDCl$_3$): δ1.11 (d, 3H), 1.96–2.16 (m, 2H), 2.02 (s, 3H), 2.11 (s, 6H), 4.06 (m, 1H), 4.61 (dd, 1H), 5.49 (bq, 1H), 6.02 (dd, 1H). MS: 215.1 (M—$C_2H_3O_2$)$^+$ Part B. Peracetyldigitoxose prepared as in Part A. above (9.31 g, 33.9 mmol) was added to 150 mL of water and 50 mL of glacial acetic acid was added. The reaction mixture was stirred at ambient temperature for 3 days. The solvent was removed in vacuo and the crude residue purified by flash chromatography (silica gel, ethyl acetate/hexanes 1:1) to give 7.37 g (94%) of a pale yellow syrup. The product, 3,4-diacetoxydigitoxose, existed as a mixture of anomers.

Part C. 3,4-Diacetoxydigitoxose (1.23 g, 5.3 mmol) was placed in a flask and 25 mL of anhydrous dichloromethane was added under a nitrogen atmosphere. Next, cesium carbonate (0.35 g, 1.1 mmol) was added followed by trichloroacetonitrile (7.2 g, 50 mmol). The reaction mixture was stirred for approximately one hour, the reaction filtered and the volatiles were removed in vacuo. The resultant crude trichloroacetimidate (2.00 g) was used crude in the subsequent reactions. $^1$H NMR (CDCl$_3$): δ1.34 (d, 3H), 2.03 (s, 3H), 2.07 (s, 3H), 2.11 (m, 1H), 2.29 (ddd, 1H), 4.17 (m, 1H), 4.80 (dd, 1H), 5.52 (m, 1H), 6.20 (dd, 1H), 8.76'(s, 1H).

Part D. Intermediate 1 (1.6 g, 3.8 mmol) was azeotroped with benzene and the dried compound was dissolved in 10 mL of dichloromethane. Anhydrous zinc bromide (0.340 g, 1.5 mmol) was added and the mixture was cooled to 0° C. A solution of the product from Part C (2.8 g, 7.5 mmol) in 5 mL of dichloromethane was added via a syringe pump over one hour. The reaction mixture was poured in aqueous sodium hydrogen carbonate solution and extracted with dichloromethane. The organic layer was dried over anhydrous sodium sulfate, filtered and the solvent removed in vacuo. The crude material was purified by flash chromatography (silica gel, ethyl acetate/hexane 1:4) to obtain 2.09 g (86%) of the desired product as a clear syrup. The product was a 2:3 mixture of α and β isomers, respectively. MS: 654.2 (M+NH$_4$)

Part E. The product from Part D (2.09 g, 3.3 mmol) was dissolved in 50 mL of methanol and potassium carbonate (0.20 g) was added. The reaction was stirred for 2 hours at ambient temperature. The potassium carbonate was removed by filtration and the volatiles removed in vacuo. The crude product was purified by flash chromatography (silica gel, eluted first with ethyl acetate/hexanes 1:2, then with ethyl acetate/hexanes 1:1) to obtain 0.84 g (49%) of the desired deacetylated β-anomer along with 0.48 g (26%) of the deacetylated α-anomer.

α-Anomer: Partial$^1$H NMR (CDCl$_3$): δ0.51 (d, 3H), 0.80 (d, 3H), 0.85–0.95 (m), 1.00 (d, 3H), 1.02 (m), 1.14 (d, 3H), 2.77 (t, 1H), 3.44 (d, 1H), 3.58 (m), 3.93 (dd, 1H), 3.27 and 3.98 (AB quartet, 2H), 4.75 (m, 1H), 5.18 (AB quartet, 2H), 6.02 (m, 1H), 7.37 (m, 5H), 9.67 (s, 1H). MS: 570.5 (M+NH$_4$)

β-Anomer: Partial$^1$H NMR (CDCl$_3$): δ0.51 (d, 3H), 0.81 (d, 3H), 0.85–1.1 (m), 1.00 (d, 3H), 1.13 (d, 3H), 2.83 (t, 1H), 3.64 (m, 1H), 3.60 and 3.87 (AB quartet, 2H), 4.10 (bs, 1H), 4.58 (dd, 1H), 5.17 (AB quartet, 2H), 6.01 (d, 1H), 7.35 (m, 5H), 9.69 (s, 1H). MS: 423.3 (M+H-digitoxose)

Part F. The β-anomer from Part E (35.6 mg) was dissolved in 3 mL of dibromomethane and 3 mL of 50% aqueous sodium hydroxide was added followed by tetrabutylammonium bromide (4.2 mg, 0.013 mmol). The mixture was stirred vigorously for 18 h. The reaction was extracted with dichloromethane and the organic phase dried over anhydrous sodium sulfate, filtered and the volatiles removed in vacuo. The residue was purified by PTLC (9:1 hexane/ethyl acetate) to obtain 16.4 mg (45%) of a white solid. Partial1H NMR (CDCl$_3$): δ0.52 (d, 3H), 0.90 (d, 3H), 0.9 (m), 1.00 (d, 3H), 1.04 (m), 1.13 (d, 3H), 2.71 (t, 1H), 3.38 (m, 1H), 3.60 and 3.89 (AB quartet, 2H), 3.64 (m, 1H), 4.13 (m, 1H), 4.48 (dd, 1H), 4.85 (s, 1H), 5.14 (s, 1H), 5.18 (AB quartet, 2H), 6.01 (d, 1H), 7.36 (m, 5H), 9.71 (s, 1H).

Part G. The product from Part F (9.7 mg, 0.017 mmol) was dissolved in 1 mL of pyridine and 1 mL of ethanol was added followed by hydroxylamine hydrochloride (12 mg, 0.17 mmol). The mixture was heated to 70° C. and stirred for 1 hour. The mixture was cooled and the solvent removed in vacuo. The residue was partitioned between water and dichloromethane and the aqueous layer extracted further with dichloromethane. The combined organic phases were dried over anhydrous sodium sulfate, filtered and the volatiles removed in vacuo. Purification of the residue by PTLC (4:1/hexane: ethyl acetate) gave 8.6 mg (87%) of the product as a solid. Partial$^1$H NMR (CDCl$_3$): δ0.52 (d, 3H), 0.81 (d, 3H), 0.9 (m), 0.98 (d, 3H), 1.01 (m), 1.23 (d, 3H), 1.34 (d, 1H), 2.62 (t, 1H), 3.36 (m, 1H), 3.60 (d, 1H), 3.64 (dd, 1H), 3.87 (d, 1H), 4.13 (m, 1H), 4.49 (dd, 1H), 4.85 (s, 1H), 5.15 (s, 1H), 5.18 (AB quartet, 2H), 5.96 (d, 1H), 7.36 (m, 5H), 7.46 (bs, 1H), 7.81 (s, 1H).

Part H. The product from Part G (8.6 mg, 0.015 mmol) was dissolved in 2 mL of toluene and Burgess' reagent (18 mg, 0.074 mmol) was added. The reaction mixture was stirred under an atmosphere of dry nitrogen at 60° C. for approximately one hour. Additional Burgess' reagent was added and the mixture was stirred an additional 20 minutes. The reaction was cooled and the volatiles were removed in vacuo. Purification of the residue by PTLC (4:1/hexane:ethyl acetate) gave 7.3 mg (86%) of the product as a solid. Partial $^1$H NMR (CDCl$_3$): δ0.39 (d, 3H), 0.88 (d, 3H), 0.95 (m), 1.14 (d, 3H), 1.23 (d, 3H), 2.62 (m, 1H), 2.72 (t, 1H), 3.36 (m, 1H), 3.59 (d, 1H), 3.63 (dd, 1H), 3.88 (d,1H), 4.11 (m, 1H), 4.48 (dd, 1H), 4.85 (s, 1H), 5.14 (s, 1H), 5.18 (AB quartet, 2H), 6.12 (m, 1H), 7.34 (m, 3H), 7.46 (m, 2H).

Part I. The product from Part H (7.3 mg, 0.013 mmol) was dissolved in 2 mL of methanol and Pearlman's catalyst (2 mg) was added. The reaction vessel was flushed with hydrogen and stirred under an atmosphere of hydrogen for 2 hours. The mixture was filtered through a pad of celite and the volatiles removed in vacuo to give 6.1 mg (100%) of the title compound as a white solid. Partial $^1$H NMR (CDCl$_3$): δ0.77 (d, 3H), 1.01 (d, 3H), 1.18 (d, 3H), 1.28 (d, 3H), 2.23 (dt, 1H), 2.35 (d, 1H), 2.67 (m, 2H), 3.39 (m, 1H), 3.54 (d, 1H), 3.63 (dd, 1H), 3.99 (m,1H), 4.15 (m, 1H), 4.57 (dd, 1H), 4.85 (s, 1H), 5.13 (s, 1H), 6.16 (d, 1H). MS: 489.2 (M+NH$_4$). IR: 2240 cm$^{-1}$

EXAMPLE 5

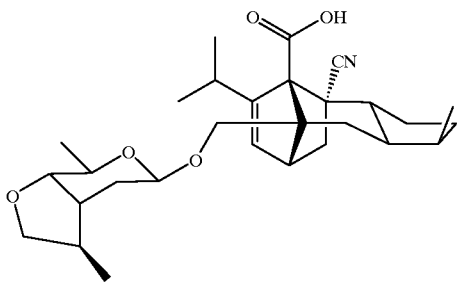

Part A. The β-anomer from Part E of Example 4 (0.84 g, 1.5 mmol) was dissolved in 100 mL of toluene. Dibutyltin oxide (0.568 g, 2.3 mmol) was added under nitrogen and the mixture was heated to reflux and stirred for 4 hours. The mixture was cooled to room temperature and allyl bromide (0.544 g, 4.5 mmol) was added followed by tetrabutylammonium fluoride (2.3 mL of a 1.0 M solution in THF, 2.3 mmol). The reaction was heated to 50° C. After 1.5 days, the mixture was cooled and the volatiles were removed in vacuo. Purification by flash chromatography (step gradient: 9:1 to 4:1 to 2:1/hexane:ethyl acetate) gave 0.454 g (51%) of a UV active product. Partial $^1$H NMR (CDCl$_3$): δ0.51 (d, 3H), 0.81 (d, 3H), 0.9 (m), 1.00 (d, 3H), 1.05 (m), 1.22 (d, 3H), 2.21 (m, 1H), 2.72 (t, 1H), 3.01 (dd, 1H), 3.60 (d, 1H), 3.68 (m, 1H), 3.87 (d, 1H), 3.98 (m, 1H), 4.10 (m, 1H), 4.18 (m, 1H), 4.59 (dd, 1H), 5.10 (m), 5.18 (AB quartet, 2H), 5.26 (d, 1H), 5.86 (m, 1H), 6.01 (d, 1H), 7.37 (m, 5H), 9.66 (s, 1H).

Part B. The product from Part A (288 mg, 0.49 mmol), triphenylphosphine (511 mg, 1.95 mmol) and imidazole (133 mg, 1.95 mmol) were placed in a flask and dissolved in 40 mL of freshly distilled tetrahydrofuran. Solid iodine (371 mg, 1.46 mmol) was added and the mixture was stirred under a nitrogen atmosphere at room temperature for 1.5 hours. 1 N Hydrochloric acid was added and the mixture was extracted with ethyl acetate. The organic phase was washed with water, sodium thiosulfate solution and then brine. The organic phase was then dried over sodium sulfate, filtered and concentrated in vacuo. The residue was purified by PTLC (9:1/hexane:ethyl acetate) to give 211 mg (61%) of the product. Partial $^1$H NMR (CDCl$_3$): δ0.51 (d, 3H), 0.80 (d, 3H), 0.9 (m), 1.00 (d, 3H), 1.05 (m), 1.33 (d, 3H), 1.22 (d, 1H), 2.51 (dd, 1H), 2.70 (t, 1H), 3.13 (t, 1H), 3.25 (m, 1H), 3.59 and 3.82 (AB quartet, 2H), 4.01 (m, 1H), 4.38 (dd, 1H), 5.18 (AB quartet, 2H), 5.20 (s, 1H), 5.30 (d, 1H), 5.96 (m, 1H), 6.00 (d, 1H), 7.37 (m, 5H), 9.69 (s, 1H). MS: 725.0 (M+Na)

Part C. To 8 mL of dry toluene was added tri-n-butyltin hydride (0.267 mL, 0.993 mmol). The solution was heated to reflux for about 2 hours. The product from Part B (211 mg, 0.301 =mol) was dissolved in 10 mL of dry toluene and added via syringe pump to the refluxing tri-n-butyltin hydride solution over 2 hours. An additional equivalent of tri-n-butyltin hydride was added added and the mixture was refluxed an additional 30 minutes at which point all of the starting material was consumed as determined by analytical TLC. The mixture was cooled and the volatiles were removed under reduced pressure. Purification by PTLC gave a yellow oil. The material was further purified by preparative HPLC (Zorbax RxC18, 5% water/95% acetonitrile, λ=220 nm) to give two products, 23.0 mg (13%) of the β-isomer and the αisomer.

β-Isomer: Partial $^1$H NMR (CDCl$_3$): δ0.50 (d, 3H), 0.80 (d, 3H), 0.89 (m), 0.98 (d, 3H), 1.02 (d, 3H), 1.20 (d, 3H), 2.22 (m, 1H), 2.72 (t, 1H), 3.29 (m, 2H), 3.58 (d, 1H), 3.65 (t, 1H), 3.82 (d,1H), 3.99 (t, 1H), 4.41 (dd, 1H), 5.19 (AB quartet, 2H), 6.01 (m, 1H), 7.36 (m, 5H), 9.72 (s, 1H).

α-Isomer: Partial $^1$H NMR (CDCl$_3$): δ0.47 (d, 3H), 0.79 (d, 3H), 0.89 (m, 1H), 0.93 (d, 3H), 0.98 (d, 3H), 1.21 (d, 3H), 2.21 (m, 1H), 2.38 (m, 1H), 2.66 (t, 1H), 3.39 (t, 1H), 3.54 (d, 1H), 3.65 (t, 1H), 3.77 (d,1H), 3.82 (t, 1H), 4.64 (m, 1H), 5.18 (s, 2H), 5.99 (m, 1H), 7.32 (m, 5H), 9.69 (s, 1H).

Part D. The β-isomer from Part C (5.6 mg, 0.0097 mmol) was dissolved in 0.5 mL of ethanol and 0.5 mL of pyridine was added followed by hydroxylamine hydrochloride (6.7 mg, 0.097 mmol). The reaction mixture was stirred under a nitrogen atmosphere for approximately 20 minutes. The mixture was concentrated under reduced pressure and partitioned between water and dichloromethane. The organic phase was dried over anhydrous sodium sulfate, filtered and concentrated in vacuo. The residue was purified by PTLC (4:1/hexane:ethyl acetate) to give 6.6 mg (quantitative) of the product. Partial $^1$H NMR (CDCl$_3$): δ0.51 (d, 3H), 0.81 (d, 3H), 0.98 (d, 3H), 1.02 (d, 3H), 1.20 (d, 3H), 2.23 (m, 1H), 2.63 (t, 1H), 3.29 (m, 2H), 3.58 (d, 1H), 3.65 (t, 1H), 3.82 (d,1H), 3.99 (t, 1H), 4.41 (dd, 1H), 5.19 (s, 2H), 5.95 (m, 1H), 7.35 (m, 5H), 7.47 (s, 1H), 7.81 (s, 1H).

Part E. The product from Part D (6.6 mg, 0.011 mmol) was dissolved in 1 mL of toluene and Burgess' Salt (13.3 mg, 0.055 mmol) was added. The mixture was stirred under nitrogen at 60° C. for 1 hour. The reaction mixture was cooled and the volatiles removed in vacuo. Purification by PTLC (9:1/hexane:ethyl acetate) gave 5.1 mg (81%) of the product. Partial $^1$H NMR (CDCl$_3$): δ0.39 (d, 3H), 0.86 (d, 3H), 1.01 (d, 3H), 1.15 (d, 3H), 1.20 (d, 3H), 2.27 (dd, 1H), 2.63 (m, 1H), 2.73 (t, 1H), 3.29 (m, 1H), 3.58 (d, 1H), 3.65 (t, 1H), 3.83 (d,1H), 3.99 (t, 1H), 4.41 (dd, 1H), 5.27 (AB quartet, 2H), 6.13 (m, 1H), 7.33 (m, 3H), 7.46 (m, 2H).

Part F. The product from Part E (5.1 mg, 0.0087 mmol) was dissolved in 1 mL of methanol and approximately 1 mg of palladium hydroxide on carbon (Pearlman's catalyst) was added. The reaction vessel was flushed with hydrogen gas and the mixture was stirred vigorously under 1 atmosphere of hydrogen for 30 minutes. The catalyst was removed by filtration through a celite pad and the filtrate was concentrated under reduced pressure to give 3.8 mg (88%) of the title compound as a white solid. Partial$^1$H NMR (CDCl$_3$): δ0.77 (d, 3H), 1.01 (d, 3H), 1.04 (d, 3H), 1.02 (d, 3H), 1.17 (d, 3H), 1.22 (d, 3H), 3.67 (t, 1H), 3.98 (t, 1H), 4.05 (d,1H), 4.55 (dd, 1H), 6.17 (m, 1H).

EXAMPLE 6

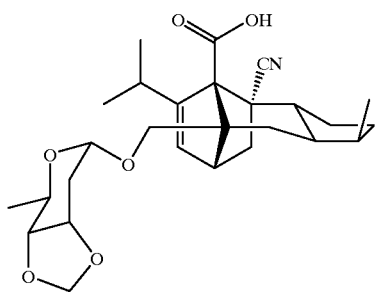

Part A. The α-anomer from Part E of Example 4 (18.3 mg, 0.033 mmol) was dissolved in 1.5 mL of dibromomethane. To the solution was added 1.5 mL of 50% aqueous sodium hydroxide followed by tetrabutylammonium bromide (2.1 mg, 0.006 mmol). The mixture was vigorously stirred for 24 hours, an additional 6 mg of tetrabutylammonium bromide was added and the mixture stirred another 24 hours. The reaction was quenched by the addition of 9.4 mL of 2 N hydrochloric acid and the mixture was partitioned between water and dichloromethane. The combined organic phases were dried over anhydrous sodium sulfate, filtered and concentrated in vacuo. The resultant residue was purified by PTLC (4:1/hexanes:ethyl acetate) to give 3.1 mg (17%) of the product. Partial$^1$H NMR (CDCl$_3$): δ0.51 (d, 3H), 0.81 (d, 3H), 0.9 (m), 1.00 (d, 3H), 1.05 (m), 1.13 (d, 3H), 2.78 (t, 1H), 3.63 (m, 2H), 3.23 and 3.91 (AB quartet, 2H), 4.05 (m, 1H), 4.62 (m, 1H), 4.94 (s, 1H), 5.13 (s, 1H), 5.18 (AB quartet, 2H), 5.99 (d, 1H), 7.35 (m, 5H), 9.69 (s, 1H).

Part B. The product from Part A (3.1 mg, 0.0055 mmol) was dissolved in 1 mL of methanol and approximately 1 mg of palladium hydroxide on carbon (Pearlman's catalyst) was added. The reaction vessel was purged with hydrogen gas and stirred under an atmosphere of hydrogen for 40 minutes. The catalyst was removed by filtration through celite. Concentration of the filtrate under reduced pressure gave 3.1 mg (quantitative yield) of the title compound. Partial$^1$H NMR (CDCl$_3$): δ0.80 (d, 3H), 0.95 (d, 3H), 1.01 (d, 3H), 1.27 (d, 3H), 2.39 (m), 2.78 (t, 1H), 3.76 (m, 4H), 4.06 (m, 1H), 4.71 (m, 1H), 4.87 (s, 1H), 5.13 (s, 1H), 6.02 (d, 1H), 9.73 (s, 1H).

EXAMPLE 7

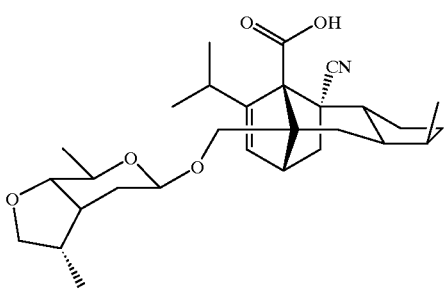

Part A. The α-isomer from Example 5, Part C (1 equivalent) is dissolved in ethanol and an equal volume of pyridine is added followed by hydroxylamine hydrochloride (10 equivalents). The reaction mixture is stirred under a nitrogen atmosphere for approximately 20 minutes or until sufficient reaction has taken place as judged by analytical TLC. The mixture is concentrated under reduced pressure and partitioned between water and dichloromethane. The organic phase is dried over anhydrous sodium sulfate, filtered and concentrated in vacuo. The residue is purified by PTLC (hexane:ethyl acetate) to give the product.

Part B. The product from Part A (1 equivalent) is dissolved in toluene and Burgess' Salt (5 equivalents) is added. The mixture is stirred under nitrogen at 60° C. for about 1 hour or until a sufficient amount of starting material has reacted. The reaction mixture is cooled and the volatiles removed in vacuo. Purification by PTLC (hexane:ethyl acetate) gives the product.

Part C. The product from Part B is dissolved in methanol and a catalytic amount of palladium hydroxide on carbon (Pearlman's catalyst) is added. The reaction vessel is flushed with hydrogen gas and the mixture is stirred vigorously under 1 atmosphere of hydrogen for about 30 minutes or until starting material has completely reacted. The catalyst is removed by filtration through a celite pad and the filtrate is concentrated under reduced pressure to give the title compound.

EXAMPLE 8

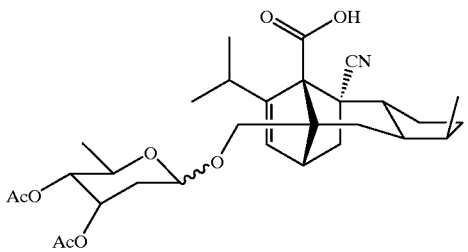

Part A. Intermediate 5 (16.3 mg, 0.039 mmol) was azeotroped with benzene three times and the dried compound along with anhydrous zinc bromide (2.0 mg, 0.0078 mmol) was added to a flask under nitrogen. Dry dichloromethane (1.0 mL) was added and the mixture was cooled to 0° C. 3,4-Diacetyldigitoxose-1-trichloroacetimidate (prepared as described in Example 4, Part C) (29.2 mg, 0.078 mmol) was dissolved in 0.075 mL of dry dichloromethane and added to the reaction mixture over a period of 1 hour. The reaction was allowed to warm to ambient temperature overnight. The mixture was poured into saturated aqueous sodium hydrogen carbonate and extracted with dichloromethane. The organic phase was dried over anhydrous sodium sulfate, filtered and the volatiles were removed in vacuo. The residue was purified by PTLC (once with 9:1 then with 4:1/hexane:ethyl acetate) to yield 17.0 mg (69%) of the product as a mixture of α- and β-isomers in a ratio of about 1:2.

Part B. The product from Part A is dissolved in methanol and palladium hydroxide on carbon (Pearlman's catalyst) is added. The reaction vessel is flushed with hydrogen gas and stirred vigorously for about 30 minutes or until no starting material remains. The catalyst is removed by filtration and the title compound is obtained upon removal of the volatiles from the filtrate. MS: 561.4 (M+NH$_4$)

EXAMPLE 9

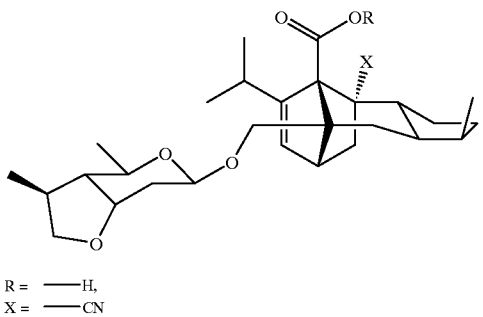

R = ——H,
X = ——CN

Part A. The compound (1 equivalent) described by the above formula but where R=—CH(C$_6$H$_5$)$_2$ and X=—CHO and whose preparation is described in WO 96/14326 is dissolved in ethanol and an equal volume of pyridine is added followed by hydroxylamine hydrochloride (10 equivalents). The reaction mixture is stirred under a nitrogen atmosphere for approximately 20 minutes or until sufficient reaction has taken place as judged by analytical TLC. The mixture is concentrated under reduced pressure and partitioned between water and dichloromethane. The organic phase is dried over anhydrous sodium sulfate, filtered and concentrated in vacuo. The residue is purified by PTLC (hexane:ethyl acetate) to give the product.

Part B. The product from Part A (1 equivalent) is dissolved in toluene and Burgess' Salt (5 equivalents) is added. The mixture is stirred under nitrogen at 60° C. for about 1 hour or until a sufficient amount of starting material has reacted. The reaction mixture is cooled and the volatiles removed in vacuo. Purification by PTLC (hexane:ethyl acetate) gives the product.

Part C. The product from Part B is dissolved in methanol and a catalytic amount of palladium hydroxide on carbon (Pearlman's catalyst) is added. The reaction vessel is flushed with hydrogen gas and the mixture is stirred vigorously under 1 atmosphere of hydrogen for about 30 minutes or until starting material has completely reacted. The catalyst is removed by filtration through a celite pad and the filtrate is concentrated under reduced pressure to give the title compound.

EXAMPLE 10

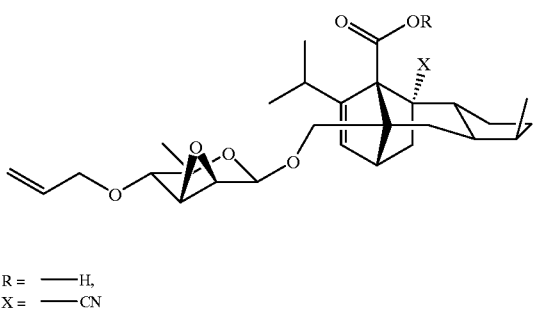

R = ——H,
X = ——CN

Part A. The compound (1 equivalent) described by the above formula but where R=—CH(C$_6$H$_5$)$_2$ and X=—CHO and whose preparation is described in WO 96/14326 is dissolved in ethanol and an equal volume of pyridine is added followed by hydroxylamine hydrochloride (10 equivalents). The reaction mixture is stirred under a nitrogen atmosphere for approximately 20 minutes or until sufficient reaction has taken place as judged by analytical TLC. The mixture is concentrated under reduced pressure and partitioned between water and dichloromethane. The organic phase is dried over anhydrous sodium sulfate, filtered and concentrated in vacuo. The residue is purified by PTLC (hexane:ethyl acetate) to give the product.

Part B. The product from Part A (1 equivalent) is dissolved in toluene and Burgess' Salt (5 equivalents) is added. The mixture is stirred under nitrogen at 60° C. for about 1 hour or until a sufficient amount of starting material has reacted. The reaction mixture is cooled and the volatiles removed in vacuo. Purification by PTLC (hexane:ethyl acetate) gives the product.

Part C. The product from Part B is dissolved in 2% trifluoroacetic acid in dichloromethane (w/w) at 0° C. and is stirred for about 4 hours or until sufficient reaction has taken place. The volatiles are removed under reduced pressure and the product purified by PTLC to give the title compound.

EXAMPLE 11

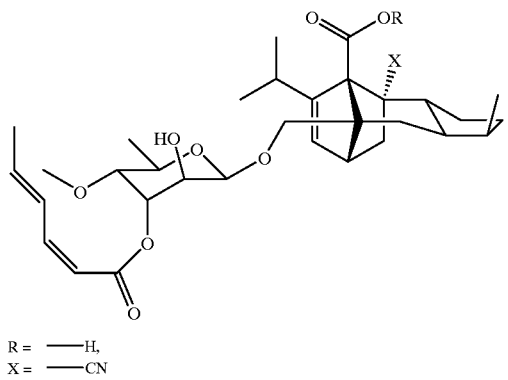

R = ——H,
X = ——CN

Part A. Zofimarin (1 equivalent) (where R=—H and X=—CHO) is dissolved in dry DMF containing 5% (v/v) p-methoxybenzyl bromide. Next, an excess of solid NaHCO$_3$ is added and the mixture is stirred at room temperature for approximately 18 hours or until a substantial amount of the zofimarin is consumed. The mixture is concentrated in vacuo and chloroform is added. The mixture is filtered to remove the NaHCO$_3$ and the filtrate is concentrated in vacuo and purified by preparative thin layer chromatogrpahy (PTLC) to yield the product where R=—CH$_2$C$_6$H$_4$-p-OCHt$_3$ and X=—CHO.

Part B. The product from Part A (1 equivalent) is dissolved in ethanol and an equal volume of pyridine is added followed by hydroxylamine hydrochloride (10 equivalents). The reaction mixture is stirred under a nitrogen atmosphere for approximately 20 minutes or until sufficient reaction has taken place as judged by analytical TLC. The mixture is concentrated under reduced pressure and partitioned between water and dichloromethane. The organic phase is dried over anhydrous sodium sulfate, filtered and concentrated in vacuo. The residue is purified by PTLC (hexane:ethyl acetate) to give the product.

Part C. The product from Part B (1 equivalent) is dissolved in toluene and Burgess' Salt (5 equivalents) is added. The mixture is stirred under nitrogen at 60° C. for about 1 hour or until a sufficient amount of starting material has reacted. The reaction mixture is cooled and the volatiles removed in vacuo. Purification by PTLC (hexane:ethyl acetate) gives the product.

Part D. The product from Part C is dissolved in 2% trifluoroacetic acid in dichloromethane (w/w) at 0° C. and is stirred for about 4 hours or until sufficient reaction has taken place. The volatiles are removed under reduced pressure and the product purified by PTLC to give the title compound.

EXAMPLES 12–19

In a manner analogous to Example 9, the following compounds may be prepared:

5,972,996

39                                                                                          40

-continued

| Starting Compound | Final Product |
|---|---|

EXAMPLES 20–22
In a manner analogous to Example 1, the following compounds may be prepared:
| Starting Compound | Final Product |
|---|---|
| | |
| | |
| | |
What is claimed is:
1. A compound having the formula I:
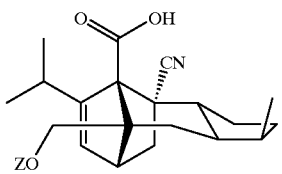
and wherein Z is a tetrahydropyrano group selected from
(a)
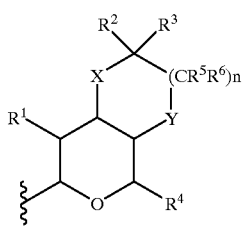
-continued
(b)
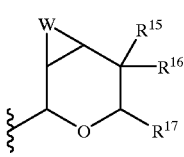
(c)
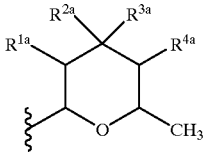
(d)
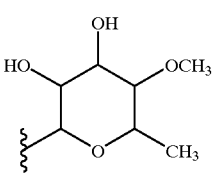

43

-continued

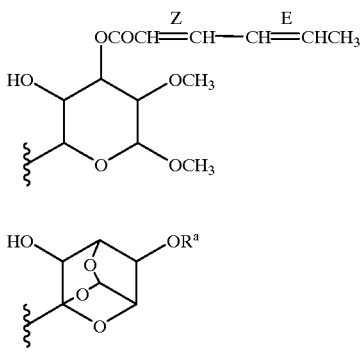

(e)

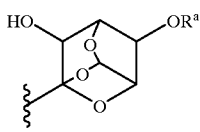

(f)

and salts and solvates (e.g. hydrates) or metabolically labile derivatives thereof,
wherein $R^a$ is C(O)CH$_3$ or CH$_3$;

$R^1$ is hydrogen, halogen, hydroxyl, $C_{1-4}$alkoxy or acyloxy;

$R^2$ and $R^3$ are each independently hydrogen, $C_{1-6}$alkyl or $C_{1-4}$alkoxy $C_{1-4}$alkyl, or $R^2$ and $R^3$ together with the carbon atom to which they are attached represent C=O, C=S or $C_{3-8}$cycloalkyl;

$R^4$ is hydrogen or CH$_2$R$^7$ (where R$^7$ is hydrogen, hydroxyl, $C_{1-4}$ alkoxy or a group OCOR$^8$ in which R$^8$ is $C_{1-4}$alkyl or aryl);

$R^5$ and $R^6$ are each independently hydrogen, $C_{1-6}$alkyl or $C_{1-4}$alkoxy $C_{1-4}$alkyl, or $R^5$ and $R^6$ together with the carbon atom to which they are attached represent C=O, C=S or $C_{3-8}$cycloalkyl;

n is zero or 1;

X and Y are each independently oxygen, sulfur or CR$^9$R$^{10}$ (where R$^9$ and R$^{10}$ are each independently hydrogen, $C_{1-6}$alkyl, $C_{1-4}$ alkoxy or $C_{1-4}$alkoxyC$_{1-14}$alkyl; or R$^9$ and R$^{10}$ together with the carbon atom to which they are attached represent C=O, C=S, $C_{3-8}$ cycloalkyl or C=CHR$^{11}$ where R$^1$ represents hydrogen or $C_{1-4}$alkyl); or when X or Y is oxygen and n is zero then —Y—CR$^2$R$^3$ or —X—CR$^2$R$^3$— respectively may also represent —N=CR$^3$— or —NR$^{12}$—CR$^2$R$^3$— (where CR$^2$ and R$^3$ are C=O and R$^{12}$ is $C_{1-4}$alkyl an acyl group COR$^{13}$ where R$^{13}$ is $C_{1-6}$alkyl) or when Y is oxygen and n is zero X may be represent the group CR$^{11}$ (wherein R$^{11}$ has the meanings defined above) which is attached to the pyran ring by a double bond;

$R^{15}$ is hydrogen, halogen, azido, $C_{1-6}$alkyl, hydroxy, $C_{1-6}$alkoxy (optionally substituted by 1 or 2 hydroxy or a ketal thereof or 1 or 2 $C_{1-3}$alkoxy groups), arylC$_{1-4}$alkoxy, $C_{3-6}$alkenyloxy, a group OCOR$^{18}$ (where R$^{18}$ is arylC$_{1-4}$alkoxy or a $C_{1-10}$alkyl group optionally containing one or two double bonds) or $C_{1-6}$ alkoxycarbonyl $C_{1-4}$alkoxy, and R$^{16}$ represents hydrogen or R$^{15}$ and R$^{16}$ may together with the carbon atom to which they are attached represent C=O or C=CH$_2$;

$R^{17}$ is CH$_2$R$^{19}$ where R$^{19}$ is hydrogen, hydroxyl, $C_{1-14}$alkoxy or a group OCOR$^{20}$ in which R$^{20}$ is $C_{1-4}$alkyl); and W is oxygen, sulfur, or CH$_2$;
and the dotted line in group (a) indicates the optional presence of an additional bond;

$R^{1a}$ is hydrogen, halogen, hydroxyl or $C_{1-4}$alkoxy;

44

$R^{2a}$ is hydrogen, halogen, hydroxyl, $C_{1-10}$alkoxy, $C_{1-10}$alkylthio, $C_{1-6}$alkoxyC$_{1-4}$alkoxy, arylC$_{1-6}$alkyloxy, arylC$_{3-6}$alkenyloxy, azido, NR$^{5a}$COR$^{5a}$ (where each R$^{5a}$ is independently hydrogen or $C_{1-6}$alkyl), OR$^{6a}$ (where R$^{6a}$ is a cyclic ether containing 4 to 8 atoms linked to the oxygen atom via a ring carbon atom adjacent to the ring oxygen atom) or a group Y$^a$C(=O)—X$^a$—R$^{7a}$ where Y$^a$ is oxygen, sulfur or NH, X$^a$ is either a bond, an oxygen atom or a moiety NR$^{8a}$ in which R$^{8a}$ is hydrogen or $C_{1-6}$alkyl, and R$^{7a}$ is $C_{1-10}$alkyl optionally containing one or two double bonds, aryl, arylC$_{1-4}$alkyl, arylC$_{2-4}$alkenyl, haloC$_{1-6}$alkyl, or $C_{1-6}$alkoxyC$_{1-4}$alkyl), and R$^{3a}$ represents hydrogen, or $R^{2a}$ and $R^{3a}$ together with the carbon atom to which they are attached represent C=O or C=NOR$^{9a}$ (where R$^{9a}$ is $C_{1-6}$alkyl); and R$^4$a is hydroxyl, $C_{1-6}$alkoxy or OC(=O)R$^{7a}$ (where R$^{7a}$ is as defined above).

2. A compound of claim 1 with the following structural formula:

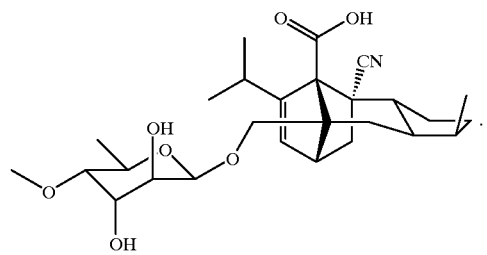

3. A compound of claim with the following structural formula:

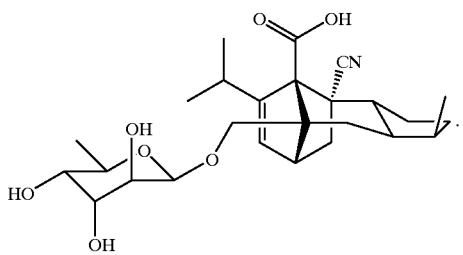

4. A compound of claim 1 with the following structural formula:

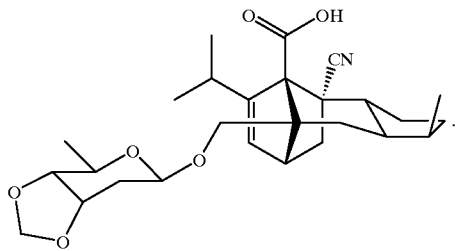

5. A compound of claim 1 with the following structural formula:

6. A compound of claim 1 with the following structural formula:

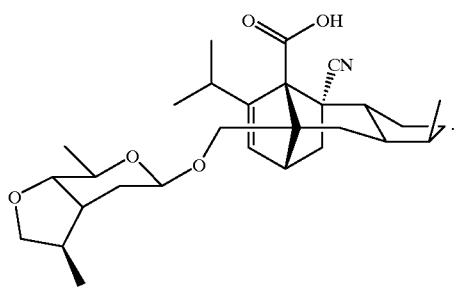

7. A compound of claim 1 with the following structural formula:

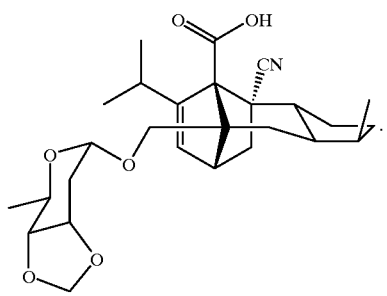

8. A compound of claim 1 with the following structural formula:

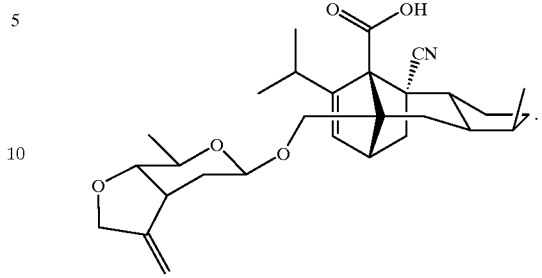

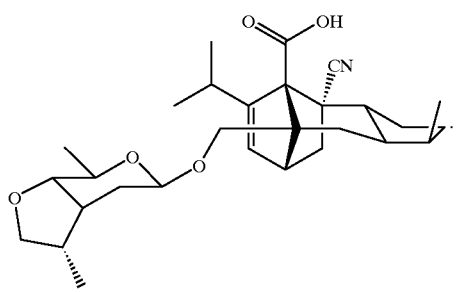

9. A pharmaceutical composition which comprises a compound of claim 1 and a pharmaceutically acceptable carrier.

10. An agrochemical composition which comprises a compound of claim 1 and a agriculturally acceptable carrier.

11. A method for the treatment or prevention of fungal infection in an animal which comprises adminstering to said animal an antifungal effective amount of a compound of claim 1.

12. A method for controlling phytopathogenic fungi which comprises administering to a plant in need of such control an antifungal effective amount of a compound of claim 1.

13. A method for the preparation of 4-cyano-4-deformyl-4'-demethyl sordarin which comprises: contacting 4-cyano-4-deformylsordarin with a culture of a strain of *Streptomyces avermitilis* in a fermentation medium containing assimilable sources of carbon and nitrogen; and isolating 4-cyano-4-deformyl-4'-demethyl sordarin from said fermentation medium.

* * * * *